(12) United States Patent
Liu et al.

(10) Patent No.: US 10,022,332 B2
(45) Date of Patent: Jul. 17, 2018

(54) STIMULI-RESPONSIVE INTERPOLYMER COMPLEX COATED HOLLOW SILICA VESICLES

(71) Applicant: AGENCY FOR SCIENCE, TECHNOLOGY AND RESEARCH, Singapore (SG)

(72) Inventors: Ye Liu, Singapore (SG); Chee Leng Lay, Singapore (SG)

(73) Assignee: Agency for Science, Technology and Research, Singapore (SG)

(*) Notice: Subject to any disclaimer, the term of this patent is extended or adjusted under 35 U.S.C. 154(b) by 59 days.

(21) Appl. No.: 14/417,107

(22) PCT Filed: Jul. 22, 2013

(86) PCT No.: PCT/SG2013/000302
§ 371 (c)(1),
(2) Date: Jan. 23, 2015

(87) PCT Pub. No.: WO2014/017981
PCT Pub. Date: Jan. 30, 2014

(65) Prior Publication Data
US 2015/0182468 A1    Jul. 2, 2015

(30) Foreign Application Priority Data
Jul. 25, 2012 (SG) ................. 201205535

(51) Int. Cl.
| | | |
|---|---|---|
| *C08F 20/06* | (2006.01) | |
| *B01J 13/22* | (2006.01) | |
| *A61K 9/50* | (2006.01) | |
| *A01N 25/28* | (2006.01) | |
| *A61K 9/51* | (2006.01) | |
| *B82Y 5/00* | (2011.01) | |
| *C09B 67/02* | (2006.01) | |
| *B82Y 40/00* | (2011.01) | |

(52) U.S. Cl.
CPC ............ *A61K 9/5031* (2013.01); *A01N 25/28* (2013.01); *A61K 9/5026* (2013.01); *A61K 9/5115* (2013.01); *A61K 9/5138* (2013.01); *B01J 13/22* (2013.01); *B82Y 5/00* (2013.01); *C08F 20/06* (2013.01); *C09B 67/0097* (2013.01); *B82Y 40/00* (2013.01)

(58) Field of Classification Search
CPC .......... B82Y 40/00; B01J 13/22; C08F 20/06; A61K 9/5026
See application file for complete search history.

(56) References Cited

U.S. PATENT DOCUMENTS

2006/0159715 A1    7/2006   Nagasaki et al.

FOREIGN PATENT DOCUMENTS

| KR | 10-2011-0115660 A | 10/2011 |
| WO | WO 2011/099932 A1 | 8/2011 |

OTHER PUBLICATIONS

Zhu, Y. et al. "Stimuli-responsive controlled drug release from a hollow mesoporous silica sphere/polyelectrolyte multilayer core-shell structure", Angew Chem 2005, 117, 5213-5217.*
PCT Notification of Transmittal of the International Search Report and the Written Opinion of the International Searching Authority, or the Declaration for PCT Counterpart Application No. PCT/SG2013/000302, 9 pgs., (dated Sep. 6, 2013).
PCT International Preliminary Report on Patentability (Chapter II of the Patent Cooperation Treaty) for PCT Counterpart Application No. PCT/SG2013/000302, 25 pgs., (dated Jun. 10, 2014).
Galiya S. Irmukhametova, et al., "Hydrogen-Bonding-Driven Self-Assembly of PEGylated Organosilica Nanoparticles with Poly(acrylic acid) in Aqueous Solutions and in Layer-by-Layer Deposition at Solid Surfaces", Langmuir, vol. 28, pp. 299-306, (2012).
Blythe Fortier-McGill, et al., "Chain Dynamics of Water-Saturated Hydrogen-Bonded Polymer Complexes and Multilayers", Macromolecules, vol. 44, pp. 2755-2765, (2011).

* cited by examiner

*Primary Examiner* — Gina C Justice
(74) *Attorney, Agent, or Firm* — Womble Bond Dickinson (US) LLP

(57) ABSTRACT

A porous hollow silica particle with an interpolymer complex immobilized thereon is provided. The interpolymer complex comprises a first polymer immobilized to a surface of the silica particle, and a second polymer complexed with the first polymer. Pharmaceutical compositions comprising the silica particle, and methods of forming the silica particle are also provided.

7 Claims, 5 Drawing Sheets

(A)

(B)

STIMULI-RESPONSIVE INTERPOLYMER COMPLEX COATED HOLLOW SILICA VESICLES

CROSS-REFERENCE TO RELATED APPLICATIONS

This patent application is a U.S. National Phase Application under 35 U.S.C. § 371 of International Application No. PCT/SG2013/000302, filed on 22 Jul. 2013, entitled STIMULI-RESPONSIVE INTERPOLYMER COMPLEX COATED HOLLOW SILICA VESICLES, which claims the benefit of priority of Singapore patent application No. 201205535-6, filed on 25 Jul. 2012, the content of which was incorporated by reference in its entirety for all purposes.

TECHNICAL FIELD

The invention relates to stimuli-responsive hollow silica vesicles or particles.

BACKGROUND

Vesicles are formed by encapsulating a volume with a thin membrane which can be composed of lipids, polymers and hybrid materials. Vesicles are important for many applications. One of the applications is for encapsulation and delivery of various species which can be for cosmetic or pharmaceuticals. Good vesicles should have 1) good stability to achieve sufficiently long shelf life for storage, and good integrity for drug delivery before reaching target sites; 2) stealth layers to provide good dispersity in aqueous solution and targeting capability; and 3) suitable fluidity for release of species encapsulated at target sites when needed.

One of the most formidable challenges in developing qualified vesicles is to address a dilemma between stability and fluidity of vesicles. Vesicles with good fluidity tend to have poor stability. For example, liposomes obtained from self-assembly of amphiphilic lipids are dynamic and feasible for species to move into and out of the vesicles. However, stability of liposomes is poor due to weak interaction among short hydrophobic lipid segments responsible for integrity of the liposomes. Even though cross-linking or formation of polymer based or silica cages may stabilize the liposomes formed, fluidity is comprised.

In comparison, structures and properties of polymer vesicles formed by self-assembly of amphiphilic copolymers may be adjusted in a wider range through tuning the chemistry, composition and molecular weight of copolymers. However, stable polymer vesicles tend to have low fluidity.

In view of the above, there remains a need to develop improved vesicles which are able to encapsulate species securely, while still being able to release the species at target sites on demand.

SUMMARY

In a first aspect, the invention refers to a porous hollow silica particle with an interpolymer complex immobilized thereon. The interpolymer complex comprises a first polymer immobilized to a surface of the silica particle, and a second polymer complexed with the first polymer.

In a second aspect, the invention refers to a pharmaceutical composition comprising a plurality of porous hollow silica particles according to the first aspect.

In a third aspect, the invention refers to a method of preparing a porous hollow silica particle with an interpolymer complex immobilized thereon. The method comprises a) providing a suspension comprising a porous hollow silica particle having a first polymer immobilized thereon;

b) adding a solution comprising a second polymer to the suspension to form a mixture; and c) adjusting the pH of the mixture to a value of less than about 5 so that the second polymer forms an interpolymer complex with the first polymer.

BRIEF DESCRIPTION OF THE DRAWINGS

The invention will be better understood with reference to the detailed description when considered in conjunction with the non-limiting examples and the accompanying drawings, in which.

Figure 1:
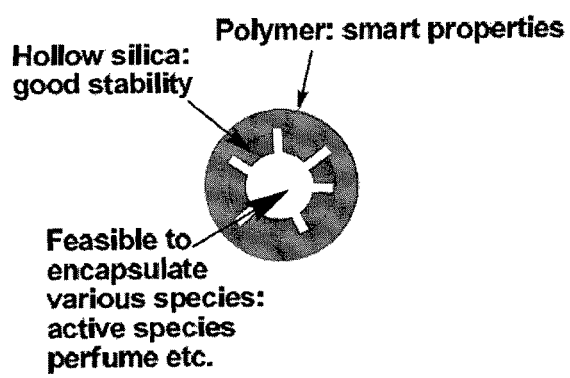
FIG. 1A is a schematic diagram depicting an interpolymer complex coated hollow silica vesicle.
FIG. 1B is a schematic diagram depicting an interpolymer complex coated hollow silica vesicle according to an embodiment under acidic and neutral conditions. In the embodiment shown, an interpolymer complex formed from PMAA and PEG (PMAA/PEG) is immobilized on a porous hollow silica particle. Under acidic conditions, the interpolymer complex forms at coating around the silica particle. When pH is increased to about 7, the interpolymer complex disassembles due to deprotonation of carboxylic acid groups in PMAA, which leads to breakdown of hydrogen bonding between the carboxylic acid groups in PMAA and the ether groups in PEG. The disassociation of the interpolymer complex on the surface of the porous hollow silica surface results in opening of the pores in the silica shell.
Figure 1:
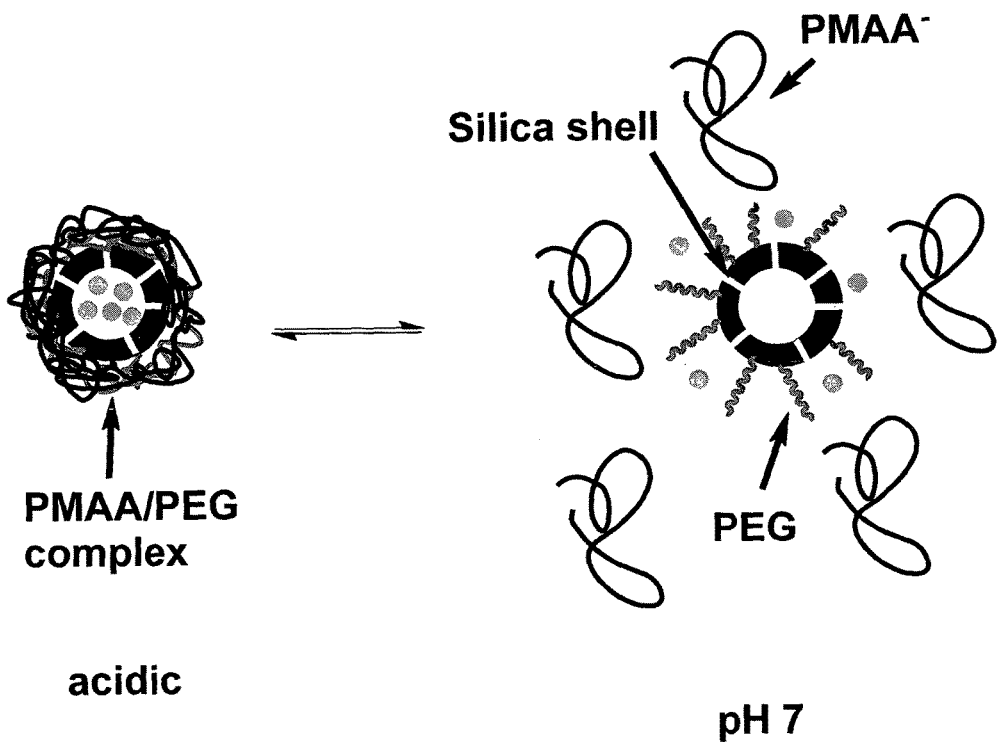

Y-axis: residual PMAA on PEG-g-hollow silica at pH 7.4 (wt %) and x-axis: time (min).

DETAILED DESCRIPTION

Interpolymer complex coated hollow silica vesicles as smart vesicles have been developed according to various embodiments. The porous silica walls of the silica particles may provide stability and feasibility to allow loading of content into and releasing of the content from the particle. The interpolymer complex layer, on the other hand, may provide stimuli-responsive properties. Depending on the pH of the environment in which the porous hollow silica particle having the interpolymer complex immobilized thereon is placed, the interpolymer complex may (i) collapse on the porous hollow silica particle to seal the pores on the particle, or (ii) dissociate to open the pores on the particle. By varying the surrounding pH, target substances may still be loaded into or unloaded from the particle. Furthermore, the interpolymer complex layer may constitute a denser layer on the hollow silica vesicles, thereby providing a more secure and stable encapsultion of the content in the particle.

Accordingly, in a first aspect the present invention refers to a porous hollow silica particle having an interpolymer complex immobilized thereon.

A porous hollow silica particle according to the first aspect consists at least essentially of silica. The void of a hollow particle is understood not to be a part of the solid particle, and is accordingly excluded from the silica content of the particle, since it generally contains matter that differs from the particle as such. Typically, the particle has a silica content of at least 90%, such as at least 94%, at least 95%, at least 96%, at least 97%, at least 98%, at least 98.5%, at least 99%, at least 99.5%, at least 99.8%, or at least 99.9%. Accordingly, the term "silica particle" as used herein may also refer to a particle that is primarily made up of silica, and which may also include a dopant such as a metal, a metal oxide, a metal salt, a metalloid a salt of a metalloid, a metalloid oxide or a non-metal element, or compound, e.g. nitrogen.

The porous hollow silica particle may be of any shape and geometry. For example, the silica particle may be a sphere, a rod, a cube, or irregularly shaped. In various embodiments, the silica particle is a sphere. As the shape of the silica particle is not always regular, e.g. perfectly spherical, size of the particle can be characterized by a maximal dimension which refers to the maximum dimension of the particle in any direction.

A silica particle according to the invention has typically a maximal width of about 1 nm to about 100 µm, such as about 1 nm to about 50 µm, about 1 nm to about 10 µm, about 2 nm to about 10 µm, about 2 nm to about 500 nm, about 2 nm to about 250 nm, about 10 nm to about 500 nm, about 10 nm to about 250 nm, about 25 nm to about 250 nm or about 50 nm to about 250 nm, such as about 250 nm, about 200 nm, about 190 nm or about 150 nm. In various embodiments, the silica particle has a maximal width in the range from about 10 nm to about 10 µm.

Depending on the maximal width, which may be in the micrometers range or nanometers range, the silica particle may respectively be termed a silica microparticle or silica nanoparticle. The silica particle microparticle or nanoparticle is a hollow micro- or nanosphere, i.e. it includes a void or cavity.

In typical embodiments, the microparticle or nanoparticle has a shell surrounding a void. The shell may be defined by a single wall with an internal and an external surface (i.e., balloon-like). The void or cavity may include the same fluid as the ambient fluid that surrounds the particle. The wall defining the shell may have a thickness of about 0.1 nm to about 1000 nm, such as about 1 nm to about 500 nm, about 1 nm to about 250 nm, about 2 nm to about 50 nm, about 5 nm to about 50 nm, about 2 nm to about 25 nm, or about 5 nm to about 20 nm, such as about 10 nm, 12 nm, 14 nm, 15 nm, or about 20 nm.

In addition to the void or cavity, the silica particle according to the first aspect has one or more pores via which the void or cavity is in fluid contact with the ambience or the surrounding environment. In various embodiments, the silica particle is microporous or mesoporous. Microporous matter is in the art understood to have pores of a width of less than about 2 nm, whereas mesoporous matter is understood as having pores of about 2 nm to about 50 nm. Size of the pores of the silica particle may be characterized by their average diameter. The term "diameter" as used herein refers to the maximal length of a straight line segment passing through the center of an area defined by a pore and terminating at the periphery. The term "average diameter" refers to an average or mean diameter of the pores, and may be calculated by dividing the sum of the diameter of each pore by the total number of pores. Although the term "diameter" is used normally to refer to the maximal length of a line segment passing through the centre and connecting two points on the periphery of a circular pore, it is also used herein to refer to the maximal length of a line segment passing through the centre and connecting two points on the periphery of pores having other shapes or an irregular shaped pore.

The silica particle may, for example, have a porous shell with pores having an average diameter in the range from about 0.1 nm to about 500 nm, such as an average diameter of about 0.1 nm to about 8 nm, about 0.5 nm to about 6 nm, about 1 nm to about 6 nm, about 1 nm to about 10 nm, about 1 nm to about 50 nm, about 1 nm to about 100 nm, about 1 nm to about 250 nm, about 1 nm to about 500 nm, or about 50 nm, about 25 nm, about 10 nm, about 5 nm, or about 1 nm. In various embodiments, the average diameter of the pores of the silica particle is in the range from about 1 nm to about 50 nm.

As mentioned above, a respective microporous or mesoporous silica particle may assume any form and shape, such as a sphere, a rod, a disc or a rope. The pores may be arranged in an ordered arrangement with symmetry such as hexagonal, cubic or lamellar. The pore volume of the silica particle is, in some embodiments, in the range from about $0.01\ cm^3/g$ to about $2\ cm^3/g$, such as from about $0.05\ cm^3/g$ to about $2\ cm^3/g$, from about $0.05\ cm^3/g$ to about $1\ cm^3/g$, from about $0.1\ cm^3/g$ to about $1\ cm^3/g$, or from about $0.1\ cm^3/g$ to about $0.5\ cm^3/g$, e.g. about $0.25\ cm^3/g$.

The characteristics of the pores of the silica particle may be analysed by a variety of techniques. Examples include, but are not limited to, transmission electron microscopy, scanning electron microscopy, gas, e.g. nitrogen, adsorption, inverse platinum replica imaging, small-angle X-ray scattering, small-angle neutron scattering and positron annihilation lifetime spectroscopy. In some embodiments of transmission electron microscopy (TEM), a series of TEM images is taken from the same position at different tilt angles and three dimensional (3D)-information obtained in the so called tomography mode. In some embodiments of scanning electron microscopy (SEM), high resolution-SEM is used, working at very low currents and voltages. Structural information may furthermore be taken from nuclear magnetic resonance (NMR), Raman and Fourier transform infrared spectroscopy (FTIR) spectroscopies, electrochemical methods, Ultraviolet-visible (UV-Vis) absorption and fluorescence spectroscopies, as well as single molecule spectroscopies. In single molecule spectroscopic methods, the materials are typically investigated by doping them with very low, usually nanomolar concentrations of fluorescent dyes. Individual molecules and/or individual nanoscale environments may then be analysed.

The wall of the silica particle may be of small or even negligible thickness in comparison to the particle dimensions, such as less than about 10%, less than about 5%, less than about 2%, or less than about 1% of the maximal particle width. The wall defining the shell may be microporous (e.g. sponge-like) in nature. Further matter may be included in the respective void or cavity, such as a fluid, including a liquid. A respective fluid included within the silica particle may in some embodiments include or consist of a pharmaceutically active compound and/or an excipient. The pharmaceutically active compound may be a low molecular weight organic compound. In some embodiments, the pharmaceutically active compound is or includes a peptide, a protein, a lipid, a saccharide or a polysaccharide. The pharmaceutically active compound may be at least substantially homogenously distributed, e.g. dispersed, within the microparticle or nanoparticle. In some embodiments, the pharmaceutically active compound is located within a certain portion of the silica microparticle or nanoparticle, such as a core or a shell.

The silica particle may have any suitable surface area that is suitable for the intended application. For example, the silica particle may have a Brunauer, Emmett and Teller (BET) surface area in the range from about 10 m$^2$/g to about 1000 m$^2$/g, such as about 25 m$^2$/g to about 500 m$^2$/g, about 50 m$^2$/g to about 250 m$^2$/g, about 75 m$^2$/g to about 200 m$^2$/g, or about 100 m$^2$/g to about 200 m$^2$/g, including a BET surface area of about 170 m$^2$/g, or about 160 m$^2$/g.

On the external surface area, i.e. the surface area on the exterior side of a shell surface of a silica particle of the invention, an interpolymer complex is immobilized thereon. The external surface area of shell-based particles may be measured by means of techniques known to those skilled in the art such as Atomic Force Microscopy (AFM) and BET isotherm analysis. The external surface area of silica particles according to the first aspect may be in the range from about 10 m$^2$/g to about 500 m$^2$/g. At least a portion of the internal surface area, i.e. the surface area facing the interior side of a shell surface of particles, may be in contact with any matter that is included in the void of the particle, such as a pharmaceutically active compound. The internal surface area of shell-based particles with contiguous solid walls cannot be measured directly via techniques such as Atomic Force Microscopy (AFM) and BET isotherm analysis, but may be estimated based on the external particle surface area and particle wall thickness.

As mentioned above, the porous hollow silica particle according to the first aspect includes an interpolymer complex immobilized thereon. The term "interpolymer complex" as used herein refers to association of macromolecules formed from two or more polymers as a result of favorable interactions between the macromolecules. Examples of favorable interactions between macromolecules include, but are not limited to hydrogen bonding, electrostatic bonding, ionic bonding, or a combination thereof. Depending on the types of macromolecules present, one or more of the above-listed interactions may be present in the interpolymer complex.

The interpolymer complex that is immobilized on the silica particle comprises a first polymer immobilized to a surface of the silica particle, and a second polymer complexed with the first polymer. In various embodiments, the interpolymer complex forms a layer around the silica particle.

The second polymer may be selected from the group consisting of poly(methacrylic acid), poly(acrylic acid), and copolymers thereof. In various embodiments, the poly (methacrylic acid) is of the general formula (1)

wherein $R_a$, $R_b$ and $R_c$ are independently an aliphatic, an alicyclic, an aromatic or an arylaliphatic group with a main chain of about 1 to about 30 carbon atoms and 0 to about 10 heteroatoms selected from the group consisting of N, O, S, Se and Si; and n is an integer from 2 to 10000; wherein all groups may be optionally substituted.

The aliphatic, alicyclic, aromatic, or arylaliphatic group may have a main chain of about 1 to about 30 carbon atoms, such as about 2 to about 30 carbon atoms, or about 2 to about 25 carbon atoms, such as about 1 to about 20 carbon atoms, about 2 to about 20 carbon atoms, about 3 to about 20 carbon atoms, about 1 to about 15 carbon atoms, about 2 to about 15 carbon atoms, about 1 to about 10 carbon atoms, about 2 to about 10 carbon atoms, about 1 to about 10 carbon atoms, or about 1 to about 6 carbon atoms, such as 1, 2, 3, 4, 5, 6, 7, 8, 9, 10, 11, 12, 13, 14, 15, 16, 17, 18, 19 or 20 carbon atoms.

The main chain of the aliphatic, alicyclic, aromatic, or arylaliphatic group may include 0 to about 10 heteroatoms, such as 0 to about 8, 0 to about 7, or 0 to about 6 heteroatoms, e.g. 0 to about 5 or 0 to about 4, including 0, 1, 2, 3, 4, 5 or 6 heteroatoms. A heteroatom is any atom other than carbon and hydrogen, such as, but not limited to N, O, S, Se, or Si.

The term "aliphatic" means, unless otherwise stated, a straight or branched hydrocarbon chain, which may be saturated and mono- or poly-unsaturated and include heteroatoms. The term "heteroatom" as used herein means an atom of any element other than carbon or hydrogen. An unsaturated aliphatic group may contain one or more double and/or triple bonds (alkenyl or alkinyl moieties). The branches of the hydrocarbon chain may include linear chains as well as non-aromatic cyclic elements. The hydrocarbon chain, which may, unless otherwise stated, be of any length, and contain any number of branches. Typically, the hydrocarbon (main) chain includes 1 to 5, to 10, to 15 or to 20 carbon atoms. Examples of alkenyl radicals are straight-chain or branched hydrocarbon radicals which contain one or more double bonds. Alkenyl radicals generally contain about two to about twenty carbon atoms and one or more, for instance two, double bonds, such as about two to about ten carbon atoms, and one double bond. Alkynyl radicals normally contain about two to about twenty carbon atoms and one or more, for example two, triple bonds, preferably such as two to ten carbon atoms, and one triple bond. Examples of alkynyl radicals are straight-chain or branched hydrocarbon radicals which contain one or more triple bonds. Examples of alkyl groups are methyl, ethyl, propyl, butyl, pentyl, hexyl, heptyl, octyl, nonyl, decyl, the n isomers of these radicals, isopropyl, isobutyl, isopentyl, sec-butyl, tert-butyl, neopentyl, or 3,3-dimethylbutyl. Both the main chain as well as the branches may furthermore contain heteroatoms as for instance N, O, S, Se or Si or carbon atoms may be replaced by these heteroatoms.

The term "alkoxy", alone or in combination, refers to an aliphatic hydrocarbon having an alkyl-O-moiety. In certain embodiments, alkoxy groups are optionally substituted. Typically, the hydrocarbon (main) chain includes 1 to 5, to 10, to 15 or to 20 carbon atoms such as 1, 2, 3, 4, or 5 carbon atoms. Examples of alkoxy groups include, but are not limited to, methoxy, ethoxy, propoxy, butoxy and the like.

The term "alicyclic" may also be referred to as "cycloaliphatic" and means, unless stated otherwise, a non-aromatic cyclic moiety (e.g. hydrocarbon moiety), which may be saturated or mono- or poly-unsaturated. The cyclic hydrocarbon moiety may also include fused cyclic ring systems such as decalin and may also be substituted with non-aromatic cyclic as well as chain elements. The main chain of the cyclic hydrocarbon moiety may, unless otherwise stated, be of any length and contain any number of non-aromatic cyclic and chain elements. Typically, the hydrocarbon (main) chain includes 3, 4, 5, 6, 7 or 8 main chain atoms in one cycle. Examples of such moieties include, but are not limited to, cyclopentyl, cyclohexyl, cycloheptyl, or cyclooctyl. Both the cyclic hydrocarbon moiety and, if present, any cyclic and chain substituents may furthermore contain heteroatoms, such as for instance N, O, S, Se or Si, or a carbon atom may be replaced by these heteroatoms. The term "alicyclic" also includes cycloalkenyl moieties that are unsaturated cyclic hydrocarbons, which generally contain about three to about eight ring carbon atoms, for example five or six ring carbon atoms. Cycloalkenyl radicals typically have a double bond in the respective ring system. Cycloalkenyl radicals may in turn be substituted. Examples of such moieties include, but are not limited to, cyclohexenyl, cyclooctenyl or cyclodecenyl.

In contrast thereto, the term "aromatic" means an at least essentially planar cyclic hydrocarbon moiety of conjugated double bonds, which may be a single ring or include multiple condensed (fused) or covalently linked rings, for example, 2, 3 or 4 fused rings. The term aromatic also includes alkylaryl. Typically, the hydrocarbon (main) chain includes 5, 6, 7 or 8 main chain atoms in one cycle. Examples of such moieties include, but are not limited to, cyclopentadienyl, phenyl, napthalenyl-, [10]annulenyl-(1,3, 5,7,9-cyclodecapentaenyl-), [12]annulenyl-, [8]annulenyl-, phenalene (perinaphthene), 1,9-dihydropyrene, chrysene (1,2-benzophenanthrene). An example of an alkylaryl moiety is benzyl. The main chain of the cyclic hydrocarbon moiety may, unless otherwise stated, be of any length and contain any number of heteroatoms, as for instance N, O and S. Such a heteroaromatic moiety may for example be a 5- to 7-membered unsaturated heterocycle having one or more heteroatoms from the series O, N, and S. Examples of such heteroaromatic moieties (which are known to the person skilled in the art) include, but are not limited to, furanyl-, thiophenyl-, naphtyl-, naphthofuranyl-, anthrathiophenyl-, pyridinyl-, pyrrolyl-, quinolinyl, naphthoquinolinyl-, quinoxalinyl-, indolyl-, benzindolyl-, imidazolyl-, oxazolyl-, oxoninyl-, oxepinyl-, benzoxe-pinyl-, azepinyl-, thiepinyl-, selenepinyl-, thioninyl-, azecinyl-, (azacyclodecapentaenyl-), diazecinyl-, azacyclododeca-1,3,5,7,9,11-hexaene-5, 9-diyl-, azozinyl-, diazocinyl-, benzazo-cinyl-, azecinyl-, azaundecinyl-, thia[11]annulenyl-, oxacyclotrideca-2,4,6,8, 10,12-hexaenyl- or triazaanthracenyl-moieties.

By the term "arylaliphatic" is meant a hydrocarbon moiety, in which one or more aromatic moieties are substituted with one or more aliphatic groups. Thus the term "arylaliphatic" also includes hydrocarbon moieties, in which two or more aryl groups are connected via one or more aliphatic chain or chains of any length, for instance, a methylene group. Typically, the hydrocarbon (main) chain includes 5, 6, 7 or 8 main chain atoms in each ring of the aromatic moiety. Examples of arylaliphatic moieties such as alkylaryl moieties include, but are not limited, to 1-ethyl-naphthalene, 1,1'-methylenebis-benzene, 9-isopropyl-anthracene, 1,2,3-trimethyl-benzene, 4-phenyl-2-buten-1-ol, 7-chloro-3-(1-methylethyl)-quinoline, 3-heptyl-furan, 6-[2-(2,5-diethyl-phenyl)ethyl]-4-ethyl-quinazoline or, 7,8-dibutyl-5,6-diethyl-isoquinoline.

Each of the terms "aliphatic", "alicyclic", "alkoxy", "aromatic" and "arylaliphatic" as used herein is meant to include both substituted and unsubstituted forms of the respective moiety. Substituents may be any functional group, as for example, but not limited to, amino, amido, azido, carbonyl, carboxyl, cyano, isocyano, dithiane, halogen, hydroxyl, nitro, organometal, organoboron, seleno, silyl, silano, sulfonyl, thio, thiocyano, trifluoromethyl sulfonyl, p-toluenesulfonyl, bromobenzenesulfonyl, nitrobenzenesulfonyl, and methane-sulfonyl.

Referring to the above general formula (1), in various embodiments $R_a$, $R_b$ and $R_c$ may be selected from the group consisting of hydrogen, methyl, ethyl and propyl. For example both $R_a$ and $R_b$ may be hydrogen, and $R_c$ may be methyl. Accordingly, the poly(methacrylic acid) may have the repeating unit

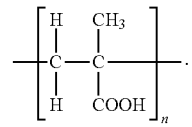

n may be an integer from 2 to about 10000, such as 0.2 to about 9000, 2 to about 8000, 2 to about 7000, 2 to about 6000, 2 to about 5000, 2 to about 4000, 2 to about 3000, 2 to about 2000, or 2 to about 1000. n may also be any integer from 2 to about 10000, and not explicitly mentioned in the above listing.

In various embodiments, the second polymer may comprise or consist of copolymers from poly(methacrylic acid) of general formula (1) and vinyl monomers of the general formula (2) $CH_2=CR_xR_y$. In formula (2), $R_x$ and $R_y$ can each be independently selected from the group consisting of H, optionally substituted aliphatic, an alicyclic, an aromatic and an arylaliphatic group with a main chain of about 1 to about 30 carbon atoms and 0 to about 10 heteroatoms selected from the group consisting of N, O, S, Se and Si.

Examples of such vinyl monomers include, but are not limited to, 1,3-butadiene, isoprene, styrene, [α]-methyl styrene, divinyl benzene, acrylonitrile, methacrylonitrile, vinyl halides such as vinyl chloride, vinyl esters such as vinyl acetate, vinyl propionate, vinyl laurate, and vinyl esters of versatic acids, heterocyclic vinyl compounds, alkyl esters of mono-olefinically unsaturated dicarboxylic acids (such as di-n-butyl maleate and di-n-butyl fumarate, fumaric acid, maleic acid, and itaconic acid, and optionally substituted alkyl esters of 1 to 20 carbon atoms thereof.

In one embodiment, the vinyl monomer may include an acrylic monomer, such as, but not limited to, methyl(meth) acrylate, ethyl(meth)acrylate, n-butyl(meth)acrylate, 2-ethylhexyl(meth)acrylate, isopropyl(meth)acrylate, n-propyl (meth)acrylate, and hydroxyalkyl(meth)acrylates such as hydroxyethyl(meth)acrylate and 2-hydroxypropyl(meth) acrylate.

The monomers may be polymerized with further monomers to form the second polymer. Such polymerization reaction may be carried out under conditions suitable to prepare a poly(methacrylic acid), a poly(acrylic acid), or a copolymer thereof. In this respect, the term "copolymer" means that the final polymer chain (made before or after attachment to the silica surface) may be made from different monomers, i.e. monomers that have different substituents $R_a$, $R_b$ and/or $R_c$ in the above formula (1) and further monomers. If desired, it is also possible to combine polymerization of monomers and attaching a pre-formed polymer to form the copolymer. By using copolymers, a further modification of the polymer chain is possible.

It should also be noted that the monomers may be present in different combinations, i.e. as alternating copolymers, periodic copolymers, statistical copolymers and/or block copolymers, wherein alternating copolymers are copolymers with regular alternating A and B units; periodic copolymers have A and B units arranged in a repeating sequence (e.g. (A-B-A-B-B-A-A-A-A-B-B-B)$_n$), statistical copolymers are copolymers in which the sequence of monomer residues follows a statistical rule, and block copolymers comprise two or more homopolymer subunits linked by covalent bonds. The union of the homopolymer subunits may require an intermediate non-repeating subunit, known as a junction block. Block copolymers with two or three distinct blocks are called diblock copolymers and triblock copolymers, respectively. In one embodiment, the second polymer is formed from three or more different copolymers, wherein one of the monomers has to be methacrylic acid.

In various embodiments, the second polymer comprises poly(methacrylic acid). In some embodiments, the second polymer consists essentially or consists of poly(methacrylic acid).

The second polymer may have a molecular weight in the range from about 3 kDa to about 150 kDa, such as about 3 kDa to about 120 kDa, about 3 kDa to about 100 kDa. about 5 kDa to about 100 kDa, about 5 kDa to about 80 kDa, about 5 kDa to about 50 kDa, about 5 kDa to about 25 kDa, about 6 kDa to about 20 kDa, about 6.5 kDa, about 15 kDa, about 30 kDa, about 60 kDa, about 100 kDa, or about 120 kDa. In various embodiments, the second polymer has a molecular weight in the range from about 3 kDa to about 8 kDa, such as about 3 kDa to about 7 kDa, about 4 kDa to about 8 kDa, about 4 kDa to about 7 kDa, about 5 kDa to about 8 kDa, about 5 kDa to about 7 kDa, or about 5 kDa, about 5.5 kDa, about 6 kDa, about 6.5 kDa, or about 7 kDa. In particular, when the second polymer consists essentially of poly(methacrylic acid), it has been surprisingly found by the inventors of the present application that poly(methacrylic acid) having a molecular weight of about 6.5 kDa results in a more compact or more dense interpolymer complex layer on the surface of the hollow silica particle.

The second polymer is complexed with the first polymer which is immobilized to a surface of the silica particle. In various embodiments, the second polymer is complexed with the first polymer by hydrogen bonding. Accordingly, in some embodiments, the first polymer is a polar polymer that is capable of forming a hydrogen bond with the second polymer. By the term "polar polymer", it refers to a polymer which contains polar functional groups such as, but is not limited to, hydroxyl group, carbonyl group, ester group, amine group, amino group, amide group, imide group, cyano group, thiol group, and carboylic acid group. Examples of polar polymers include polyesters, polyamides, polyimides, polyacrylic acids, polyethers, polyether block amides, polyetheramides, polyetherimides, polycarbonates, polyphenyleneoxides, polyvinylalcohols and polyvinylchlorides.

In various embodiments, the first polymer is selected from the group consisting of poly(ethylene glycol), poly(vinyl pyrrolidone), chitosan, derivatives thereof, and copolymers thereof. In various embodiments, the first polymer comprises poly(ethylene glycol). In some embodiments, the first polymer consists essentially of or consists of poly(ethylene glycol).

The first polymer is immobilized on a surface of the silica particle. In some embodiments, the first polymer may be attached directly to the silica surface. For example, in case the silica surface carries functional groups (coupling groups) such as —OH, —NH$_2$ or halogen groups, the direct linkage is possible.

In other embodiments, the first polymer is immobilized on or grafted to the silica surface via a bridging group. Generally, the bridging group may be any molecule that is capable of linking the first polymer to the silica surface. As an example, amino groups or halogen groups may be introduced on the surface of the silica particle, for example, via coupling of an amino-functional or halogen-functional alkylsilane or siloxane, such as N-(3-trimethoxysilyl) propyl ethylene diamines (TMSPEA). In various embodiments, the bridging group is selected from the group consisting of aminoalkyl silane, halogenalkyl silane, and aminoalkoxy silane.

A porous hollow silica particle with an interpolymer complex immobilized thereon is obtained. Typically the interpolymer complex defines a coating on the surface of the hollow silica particle. As mentioned above, the interpolymer complex forms a particularly high density coating on the silica particle. The silica particle may have a polymer content in the range from about 50% to about 90% (w/w). In various embodiments, the silica particle has a polymer content in the range from about 50% to about 90% (w/w), such as about 50% to about 80% (w/w), about 50% to about 70% (w/w), about 50% to about 60% (w/w), about 60% to about 90% (w/w), about 60% to about 80% (w/w), about 60% to about 70% (w/w), about 70% to about 90% (w/w), about 70% to about 80% (w/w), about 55% to about 85% (w/w), or about 65% to about 85% (w/w). Typically, the silica particle has a polymer content of at least about 50% (w/w), including at least about 55% (w/w), at least about 60% (w/w), at least about 65% (w/w), at least about 70% (w/w), or at least about 75 (w/w).

The values listed above refer to the total polymer content, i.e. an aggregate of the first polymer and the second polymer content on the silica particle. In various embodiments, the amount of first polymer on the silica particle is in the range from about 35% to about 60% (w/w), such as about 35% to about 55% (w/w), about 35% to about 50% (w/w), about 35% to about 45% (w/w), about 40% to about 60% (w/w), about 45% to about 60% (w/w), about 35% (w/w), about 40% (w/w), about 45% (w/w), or about 50% (w/w). In embodiments wherein the first polymer consists essentially of polyethylene glycol (PEG), the amount of PEG on the silica particle surface is about 46% (w/w).

The amount of second polymer on the silica particle may be in the range from about 15% to about 30% (w/w), such as about 15% to about 25% (w/w), about 15% to about 20% (w/w), about 20% to about 30% (w/w), about 20% to about 25% (w/w), about 15% (w/w), about 20% (w/w), about 25% (w/w), or about 30% (w/w). In embodiments wherein the second polymer consists essentially of poly(methacrylic acid) (PMAA), the amount of PMAA on the silica particle surface is about 21 to about 23% (w/w).

The interpolymer complex, which may be present as a layer on the silica particle, provide pH responsive properties. Depending on the pH of the environment within which the silica particle is placed, the structure of the interpolymer complex layer may assume a closed or collapsed structure in which the pores of the silica particle are covered, or an open structure in which the pores of the silica particle are not covered. Under acidic conditions where pH is at a low value of, for example, below 5.0, below 4.5, below 4.0, below 3.5, below 3.0 or below 2.0, the second polymer may be complexed with the first polymer that is immobilized to a surface of the silica particle, such that pores of the silica particle are covered. Thus, at acidic condition, the shrunk or collapsed interpolymer complex, which may form a layer around the silica particle, seals the pores in the silica shells to prevent the release of the species encapsulated in the porous hollow silica particle. Generally, the pH value may be less than or equal to 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9 or 5.0. "Collapsed" in this respect means that the interpolymer complex layer assumes a closed and compact configuration around the silica particle. In various embodiments, the pores of the silica particle are sealed at a pH of less than about 5.

At relatively high pH values, the second polymer may dissociate from the first polymer, thereby exposing the pores of the silica particle. The pH value of such a solution may be, but not limited to, above 5, such as above 5.5, above 6.0, above 6.5 or above 7.0. Generally, the pH value at which the polymer is soluble may be greater than or equal to 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4 or 7.5. In various embodiments, the pores of the silica particle are opened at a pH of more than about 5.

The hollow silica particles may be used as carriers for pharmaceuticals or for drug delivery purposes. Any pharmaceutically active compound may be included into the particles. The pharmaceutically active compound may be present in the inner void of the silica particle. In various embodiments, such a compound is polar and water-soluble. In some embodiments the compound is amphiphilic. In some embodiments, the compound is at least essentially non-polar and water-insoluble. The pharmaceutically active compound may be a low molecular weight organic compound. In some embodiments, the pharmaceutically active compound is or includes a peptide, a protein, a peptoid, a lipid, a nucleic acid, a saccharide, an oligosaccharide, a polysaccharide or an inorganic molecule.

The pharmaceutically active compound may be at least substantially homogenously distributed or dispersed within the hollow microparticle or nanoparticle. In some embodiments, the pharmaceutically active compound is located within a certain portion of the silica microparticle or nanoparticle, such as a nanoparticle or the inner wall of a shell of the hollow particle. When provided in a hollow particle, compounds may be protected from the action of components of the ambience such as enzymes, e.g. proteases, in case the pH value is below 5.0. In particular, where the particle transiently passes a tissue or organ, e.g. the digestive tract, the particle thereby provides protection from degradation or modification. Nevertheless, a compound may be provided in the hollow particle in the form of a prodrug if desired.

Further, the particle may be used, for example, to direct the compound to a desired target or site of action by providing corresponding moieties on the surface of the particle. In such embodiments, the application resembles rather a local than a systemic application. Using a particle to encompass a compound also allows the application of a compound that can otherwise hardly be applied via standard application routes, such as an at least essentially non-polar compound. In addition, depending on the selection of the pore size, particle size and other structural features of the particle, the particle provides a diffusion barrier as well as a protection from flow and abrupt changes of the ambience. Therefore, encompassing matter such as pharmaceutically active compounds in a hollow particle, e.g. a particle with pores, slows the release of matter therefrom. Accordingly, the half-life of compounds in the human or animal body can be controlled by selecting the structural properties of the particle. Typically the half-life of compounds in the human or animal body is longer when applied in a hollow particle.

As used herein, the term "prodrug" means a compound which is converted or released within the human or animal body, e.g. enzymatically, mechanically or electromagnetically, into its active form that has medical effects. A "prodrug" is accordingly a pharmacologically inactive derivative of a parent "drug" molecule. It requires spontaneous or enzymatic biotransformation within the physiological system of the human or animal to which it is administered. "Prodrugs" are commonly used in the art to overcome problems associated with stability, toxicity, lack of specificity, or limited bioavailability. They often offer advantages of solubility, tissue compatibility, or delayed release in the mammalian organism. As an illustrative example, a "prodrug" may be a low molecular weight compound with a protective group shielding a moiety or functional group thereof and thereby reversibly suppressing the activity of the functional group. A respective "prodrug" may become pharmaceutically active in vivo or in vitro when the protective group undergoes solvolysis or enzymatic removal. As a further illustrative example, a functional group may only be introduced into a compound of general formula (1) upon biochemical transformation such as oxidation, phosphorylation, or glycosylation. Thus a respective "prodrug" may only be converted into a compound of general formula (1) by an enzyme, gastric acid, etc. in the human or animal body. The "prodrug" of a compound of general formula (1) may be a hydrate or a non-hydrate. Common "prodrugs" include acid derivatives such as esters prepared by reaction of parent acids with a suitable alcohol (e.g., a lower alkanol), amides prepared by reaction of the parent acid compound with an amine (e.g., as described above), or basic groups reacted to form an acylated base derivative (e.g., a lower alkylamide).

In this regard, in a second aspect, the invention also provides a pharmaceutical composition. The pharmaceutical composition includes one or more porous hollow silica particles according to the first aspect. The porous hollow silica particle may have a pharmaceutically active compound in the void of the hollow particle. As detailed above, the void may be encompassed by a shell that surrounds the void. The particles that are included in the pharmaceutical composition may be water-soluble. Generally, a silica particle is rendered water-soluble by selecting an appropriate interpolymer complex for immobilization thereon.

In various embodiments, a respective silica particle according to the first aspect is coupled to a molecule with binding affinity for a selected target tissue or for a selected target molecule, such as a microorganism, a virus particle, a peptide, a peptoid, a protein, a nucleic acid, a peptide, an oligosaccharide, a polysaccharide, an inorganic molecule, a synthetic polymer, a small organic molecule or a drug.

Illustrative examples of a molecule with binding affinity for a certain target are an antibody, a fragment thereof and a proteinaceous binding molecule with antibody-like functions. Examples of (recombinant) antibody fragments are Fab fragments, Fv fragments, single-chain Fv fragments (scFv), diabodies, triabodies, decabodies, and other domain antibodies. An example of a proteinaceous binding molecule with antibody-like functions is a mutein based on a polypeptide of the lipocalin family. Lipocalins, such as the bilin binding protein, the human neutrophil gelatinase-associated lipocalin, human Apolipoprotein D or glycodelin, posses natural ligand-binding sites that can be modified so that they bind to selected small protein regions known as haptens. Examples of other proteinaceous binding molecules are the so-called glubodies, proteins based on the ankyrin scaffold, or crystalline scaffold, AdNectins, tetranectins and avimers. Avimers contain so called A-domains that occur as strings of multiple domains in several cell surface receptors. Adnectins, derived from a domain of human fibronectin, contain three loops that can be engineered for immunoglobulin-like binding to targets. Tetranectins, derived from the respective human homotrimeric protein, likewise contain loop regions in a C-type lectin domain that can be engineered for desired binding. Peptoids, which can act as protein ligands, are oligo(N-alkyl)glycines that differ from peptides in that the side chain is connected to the amide nitrogen rather than the α carbon atom. Peptoids are typically resistant to proteases and other modifying enzymes and can have much higher cell permeabilities than peptides.

As a further illustrative example, a linking moiety such as an affinity tag may be used to immobilise a molecule with binding affinity for a selected target tissue or for a selected target molecule. Such a linking moiety may be a molecule, e.g. a hydrocarbon-based (including polymeric) molecule that includes nitrogen-, phosphorus-, sulphur-, carben-, halogen- or pseudohalogen groups, or a portion thereof. As an illustrative example, the silica surface may include functional groups. Such functional groups may be residual groups, e.g. amino groups, used and/or provided for the covalent attachment of the polymer, and which did not undergo a coupling reaction therewith. These groups may allow for the covalent attachment of a biomolecule, for example a molecule such as a protein, a nucleic acid molecule, a polysaccharide or any combination thereof.

Examples of an affinity tag include, but are not limited to biotin, dinitrophenol or digoxigenin, oligohistidine, polyhistidine, an immunoglobulin domain, maltose-binding protein, glutathione-S-transferase (GST), calmodulin binding peptide (CBP), FLAG'-peptide, the T7 epitope (Ala-Ser-Met-Thr-Gly-Gly-Gln-Gln-Met-Gly), maltose binding protein (MBP), the HSV epitope of the sequence Gln-Pro-Glu-Leu-Ala-Pro-Glu-Asp-Pro-Glu-Asp of herpes simplex virus glycoprotein D, the hemagglutinin (HA) epitope of the sequence Tyr-Pro-Tyr-Asp-Val-Pro-Asp-Tyr-Ala, the "myc" epitope of the transcription factor c-myc of the sequence Glu-Gln-Lys-Leu-Ile-Ser-Glu-Glu-Asp-Leu, or an oligonucleotide tag. Such an oligonucleotide tag may for instance be used to hybridise to an immobilised oligonucleotide with a complementary sequence. A further example of a linking moiety is an antibody, a fragment thereof or a proteinaceous binding molecule with antibody-like functions (see also above).

A further example of a linking moiety is a cucurbituril or a moiety capable of forming a complex with a cucurbituril. A cucurbituril is a macrocyclic compound that includes glycoluril units, typically self-assembled from an acid catalyzed condensation reaction of glycoluril and formaldehyde. A cucurbit[n]uril, (CB[n]), that includes n glycoluril units, typically has two portals with polar ureido, carbonyl groups. Via these ureido carbonyl groups cucurbiturils can bind ions and molecules of interest. As an illustrative example cucurbit[7]uril (CB[7]) can form a strong complex with ferrocenemethylammonium or adamantylammonium ions. Either the cucurbit[7]uril or e.g. ferrocenemethylammonium may be attached to a biomolecule, while the remaining binding partner (e.g. ferrocenemethylammonium or cucurbit[7]uril respectively) can be bound to a selected surface. Contacting the biomolecule with the surface will then lead to an immobilisation of the biomolecule. Functionalised CB[7] units bound to a gold surface via alkanethiolates have for instance been shown to cause an immobilisation of a protein carrying a ferrocenemethylammonium unit.

Further examples of a linking moiety include, but are not limited to an oligosaccharide, an oligopeptide, biotin, dinitrophenol, digoxigenin, or a metal chelator. As an illustrative example, a respective metal chelator, such as ethylenediamine, ethylene-diaminetetraacetic acid (EDTA), ethylene glycol tetraacetic acid (EGTA), diethylenetri-aminepentaacetic acid (DTPA), N,N-bis(carboxymethyl)glycine (also called nitrilotriacetic acid, NTA), 1,2-bis(o-aminophenoxy)ethane-N,N,N',N'-tetraacetic acid (BAPTA), 2,3-dimercapto-1-propanol (dimercaprol), porphine or heme may be used in cases where the target molecule is a metal ion. As an example, EDTA forms a complex with most monovalent, divalent, trivalent and tetravalent metal ions, such as e.g. silver ($Ag^+$), calcium ($Ca^{2+}$), manganese ($Mn^{2+}$), copper ($Cu^{2+}$), iron ($Fe^{2+}$), cobalt ($Co^{3+}$), and zirconium ($Zr^{4+}$), while BAPTA is specific for $Ca^{2+}$. In some embodiments, a respective metal chelator in a complex with a respective metal ion or metal ions defines the linking moiety. Such a complex is for example a receptor molecule for a peptide of a defined sequence, which may also be included in a protein. As an illustrative example, a standard method used in the art is the formation of a complex between an oligohistidine tag and copper ($Cu^{2+}$), nickel ($Ni^{2+}$), cobalt ($Co^{2+}$), or zinc ($Zn^{2+}$) ions, which are presented by means of the chelator nitrilotriacetic acid (NTA). Avidin or streptavidin may for instance be employed to immobilise a biotinylated nucleic acid, or a biotin containing monolayer of gold may be employed.

A molecule or moiety immobilized on the porous particulate material may also serve in cross-linking individual particles. An organic bridge may for instance be formed between two particles by a phenylene-bridge or an ethylene-bridge. The bridge may also include a chiral moiety such as bulk vanadyl Schiff base complexes, a binaphthyl group, a 1,2-diaminocyclohexane group, a trans-(1R,2R)-bis-(ureido)-cyclohexyl-bridge, or a chiral borated ethylene-bridge. The resulting particulate matter is a chiral porous material with chiral induction ability in e.g. asymmetric catalysis. A further example of a chiral moiety that may be immobilized on the porous particulate material is a carbohydrate, including a cellulose derivative such as cellulose tris(3,5-dimethylphenyl carbamate).

In a third aspect, the invention refers to a method of preparing a porous hollow silica particle with an interpolymer complex immobilized thereon. The method comprises providing a suspension comprising a porous hollow silica particle having a first polymer immobilized thereon. Examples of polymers which may be used to form the first polymer, and ways in which the first polymer may be immobilized on the surface of the silica particle have already been described above.

In various embodiments, providing a suspension comprising a porous hollow silica particle having a first polymer immobilized thereon includes functionalizing the silica surface with a functional group such as an amino or a halogen group.

The process of providing amino or halogen functional groups on the silica surface may be carried out at ambient temperature or at an elevated temperature, i.e. a temperature above ambient temperature. The temperature may for example be selected in the range from about 30° C. to about 150° C., about 30° C. to about 120° C., about 40° C. to about 100° C. or about 50° C. to about 100° C., e.g. about 50° C., about 60° C., about 70° C., about 80° C., about 90° C. or about 100° C. The process may also be carried out under an inert gas atmosphere, i.e. in the presence of gases that are not reactive, or at least not reactive to a detectable extent, with regard to the reagents and solvents used. Examples of a reactive inert atmosphere are nitrogen, or a noble gas such as argon or helium.

The surface of silica particle that carries a functional group, such as amino functional group, is contacted with the first polymer under suitable conditions to graft the first polymer to the surface of the silica particle. The process of coupling the first polymer to the silica surface may, in some embodiments, be carried out under an inert gas atmosphere. The process may be carried out at room temperature or at an elevated temperature. The temperature may, for example, be selected in the range from about 30° C. to about 120° C., about 40° C. to about 100° C. or about 50° C. to about 100° C., e.g. about 50° C., about 60° C., about 70° C., about 80° C., about 90° C. or about 100° C.

The process may also be carried out under an inert gas atmosphere, i.e. in the presence of gases that are not reactive, or at least not reactive to a detectable extent, with regard to the reagents and solvents used. Examples of a reactive inert atmosphere are nitrogen or a noble gas such as argon or helium. The process may take up to several days, such as about 24 hours, about 36 hours, about 48 hours, about 60 hours or about 72 hours.

The method according to the third aspect is generally carried out in the liquid phase. It may be carried out in any suitable solvent, which may be polar or non-polar liquids, including aprotic non-polar liquids. Examples of non-polar liquids include, but are not limited to, mineral oil, hexane, heptane, cyclohexane, benzene, toluene, pyridine, dichloromethane, chloroform, carbon tetrachloride, carbon disulfide and a non-polar ionic liquid. Examples of a non-polar ionic liquid include, but are not limited to, 1-ethyl-3-methylimidazolium bis[(trifluoromethyl)sulfonyl]amide bis(triflyl)amide, 1-ethyl-3-methylimidazolium bis[(trifluoromethyl)sulfonyl]amide trifluoroacetate, 1-butyl-3-methylimidazolium hexafluorophosphate, 1-hexyl-3-methylimidazolium bis(trifluoromethylsulfonyl)imide, 1-butyl-3-methylimidazolium bis(trifluoromethylsulfonyl)imide, trihexyl(tetradecyl)phosphonium bis[oxalato(2-)]borate, 1-hexyl-3-methyl imidazolium tris(pentafluoroethyl)trifluorophosphate, 1-butyl-3-methyl-imidazolium hexafluorophosphate, tris(pentafluoroethyl)trifluorophosphate, trihexyl(tetradecyl)phosphonium, N"-ethyl-N,N,N', N'-tetramethylguanidinium, 1-butyl-1-methyl pyrroledinium tris(pentafluoroethyl)trifluorophosphate, 1-butyl-1-methyl pyrrolidinium bis(trifluoromethylsulfonyl)imide, 1-butyl-3-methyl imidazolium hexafluorophosphate, 1-ethyl-3-methylimidazolium bis-(trifluoromethylsulfonyl)imide and 1-n-butyl-3-methylimidazolium.

In some embodiments, the method is carried out in a polar solvent. Examples of a polar solvent include, but are not limited to, dioxane, diethyl ether, diisopropylether, ethylene glycol monobutyl ether, tetrahydrofuran, methyl propyl ketone, methyl isoamyl ketone, methyl isobutyl ketone, cyclohexanone, isobutyl isobutyrate, ethylene glycol diacetate, and a polar ionic liquid. Examples of a polar ionic liquid include, but are not limited to, 1-ethyl-3-methylimidazolium tetrafluoroborate, N-butyl-4-methylpyridinium tetrafluoroborate, 1,3-dialkylimidazolium-tetrafluoroborate, 1,3-dialkylimidazolium-hexafluoroborate, 1-ethyl-3-methylimidazolium bis(pentafluoroethyl)phosphinate, 1-butyl-3-methylimidazolium tetrakis-(3,5-bis(trifluoromethylphenyl) borate, tetrabutyl-ammonium bis(trifluoromethyl)imide, ethyl-3-methylimidazolium trifluoromethanesulfonate, 1-butyl-3-methylimidazolium methyl-sulfate, 1-n-butyl-3-methylimidazolium ([bmim]) octylsulfate, and 1-n-butyl-3-methylimidazolium tetrafluoroborate.

The method of the third aspect comprises adding a solution comprising a second polymer to the suspension to form a mixture. Examples of polymers which may be used as the second polymer have already been described above. The method includes adjusting the pH of the mixture to a value of less than about 5, so that the second polymer forms an interpolymer complex with the first polymer. In various embodiments, the second polymer is complexed with the first polymer by hydrogen bonding.

The method may further comprise adding a target substance to be encapsulated into the mixture prior to adjusting the pH of the mixture to a value of less than about 5 for forming an interpolymer complex between the first polymer and the second polymer. The target substance may be added to the suspension comprising a porous hollow silica particle or to the solution comprising the second polymer. In various embodiments, the target substance is added to the solution comprising the second polymer.

Examples of target substance include, but are not limited to, a drug, a protein, such as an enzyme and an antibody; a peptide, a growth factor, an organic molecule, a nucleic acid, a pesticide, a dye, and a fertilizer.

In various embodiments the target substance is a drug. Accordingly, particles according to the invention may be used as a carrier for a drug, a marker, or other matter to be administered to a human or animal body. The micro- or nanoparticles described herein, as well as matter such as compounds included therein, may be administered to a cell, an animal or a human patient per se, or in a pharmaceutical composition.

In a pharmaceutical composition, the particles may be mixed with other active ingredients, as in combination therapy, or with suitable carriers or excipient(s). Techniques for formulation and administration of respective particles resemble or are identical to those of low molecular weight compounds established in the art. Exemplary routes include, but are not limited to, oral, transdermal, and parenteral delivery. A plurality of the particles may be used to fill a capsule or tube, or may be compressed as a pellet. The micro- or nanoparticles may also be used in injectable or sprayable form, for instance as a suspension or in a gel formulation.

The pharmaceutical composition including the hollow silica particles according to an aspect of the invention offers great advantages for the administration of pharmaceutical compounds. Due to the pH sensitivity, the encapsulated drug is not released, for example, by the gastric acid (pH below about 5.0) in the stomach, i.e. there is no significant drug leakage in the stomach as the interpolymer complex immobilized on a surface of the silica particle is "collapsed" and the pores of the silica particle are closed. The drug is protected so that no degradation or modification of the active compound takes place. Once the drug passes to the intestine, the pH value of the environment raises to above about 5.0 or more. As explained above, the second polymer that is complexed with the first polymer dissociates from the first polymer, such that the pores of the silica particle are opened to allow release of the drugs contained therein.

In various embodiments, the silica particles according to the first aspect may be used to formulate various drug systems, especially for oral delivery of drugs. The pH responsive properties of the silica vesicles may, for example, be suitable for delivery of sensitive drugs, for example, proteinaceous drugs such as insulin or acid labile drugs. In the acidic stomach, the shrunk interpolymer complex layer protects such drugs, for example, insulin from degradation by enzyme, and in intestine, the interpolymer complex layer dissociates to allow release of insulin from the particle. Besides the above, the hollow silica vesicles may, for example, be applied to formulate immunosupressants such as cyclosporine A to thereby provide more predictable bioavailability of cyclosporine A.

Suitable routes of administration may, for example, include depot, oral, rectal, transmucosal, or intestinal administration; parenteral delivery, including intramuscular, subcutaneous, intravenous, intramedullary injections, as well as intrathecal, direct intraventricular, intraperitoneal, intranasal, or intraocular injections. It is noted in this regard that for administering micro- or nanoparticles, a surgical procedure is not required. The route of administration depends on the one hand on the pharmaceutical used and on the other hand on the conditions present at the administration site. This means, the conditions at the administration site or at the site the pharmaceutical is delivered have to be in such a way that the interpolymer complex is able to dissociate and the pores of the silica vesicle are open. Generally, the interpolymer complex may be further adapted by varying the types of polymers that are used to form the complex in order to achieve the respective properties. In one embodiment, the administration route is by oral.

Alternately, one may administer the particles in a local rather than systemic manner, for example, via injection of the compound directly into a solid tumour, often in a depot or sustained release formulation.

Pharmaceutical compositions that include the particles described herein may be manufactured by means of conventional mixing, dissolving, granulating, dragee-making, levigating, emulsifying, encapsulating, entrapping or lyophilizing processes. Pharmaceutical compositions for use in accordance with various aspects described herein may thus be formulated in conventional manner using one or more physiologically acceptable carriers including excipients and auxiliaries that facilitate processing of the particles into preparations that can be used pharmaceutically. Proper formulation is dependent upon the route of administration chosen.

For injection, the particles of the invention may be formulated in aqueous solutions, for instance in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the micro- or nanoparticles can be formulated readily by combining them with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatine, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that may be used orally include push-fit capsules made of gelatine, as well as soft, sealed capsules made of gelatine and a plasticizer, such as glycerol or sorbitol. The push-fit capsules may contain the active ingredients in admixture with filler such as lactose, binders such as starches, and/or lubricants such as talc or magnesium stearate and, optionally, stabilizers. In soft capsules, the particles may be suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

The micro- or nanoparticles may be formulated for parenteral administration by injection, e.g., by bolus injection or continuous infusion. Formulations for injection may be presented in unit dosage form, e.g., in ampules or in multidose containers, with an added preservative. The compositions may take such forms as suspensions, solutions or emulsions in oily or aqueous vehicles, and may contain formulatory agents such as suspending, stabilizing and/or dispersing agents.

Pharmaceutical compositions suitable for use in the present invention include compositions where the active ingredients included in the micro- or nanoparticles are contained in an amount effective to achieve its intended purpose. Determination of a therapeutically effective amount is well within the capability of those skilled in the art, especially in light of the detailed disclosure provided herein.

For any compound used in the micro- or nanoparticles of the invention, the therapeutically effective dose may be estimated initially from cell culture assays. For example, a dose may be formulated in animal models to achieve a circulating concentration range that includes the $IC_{50}$ as determined in cell culture (i.e., the concentration of the test compound which achieves a half-maximal inhibition of the kinase activity). Such information may be used to more accurately determine useful doses in humans.

The micro- or nanoparticles may, if desired, be presented in a pack or dispenser device which may contain one or more unit dosage forms containing the particles with the active ingredient. The pack may for instance include metal or plastic foil, such as a blister pack. The pack or dispenser device may be accompanied by instructions for administration. The pack or dispenser may also be accompanied with a notice associated with the container in a form prescribed by a governmental agency regulating the manufacture, use, or sale of pharmaceuticals, which notice is reflective of approval by the agency of the form of the compound for human or veterinary administration. Such notice, for example, may be the labeling approved by the U.S. Food and Drug Administration or other government agency for prescription drugs, or the approved product insert.

Hereinafter, the present invention will be described more fully with reference to the accompanying drawings, in which exemplary embodiments of the invention are shown. This invention may, however, be embodied in many different forms and should not be construed as limited to the exemplary embodiments set forth herein. Rather, these embodiments are provided so that this disclosure will be thorough and complete, and will fully convey the scope of the invention to those skilled in the art. In the drawings, lengths and sizes of layers and regions may be exaggerated for clarity.

As used herein, the term "and/or" includes any and all combinations of one or more of the associated listed items. It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Example 1: Preparation of Hollow Silica Particles

Hollow silica can be prepared using polystyrene colloids as templates of sol-gel reaction of tetraethoxysilane (TEOS) followed by calcinations.

In a typical process, 3.0 g of poly(vinyl-pyrrolidone) (PVP) (Mw: 40 K) was dissolved in 100 mL of HPLC grade water under stirring for 24 h at room temperature. Then 11.0 mL of styrene and 0.26 g of α,α'-azodiisobutyramidine dihydrochloride (AIBA) were added to the solution under stirring at 100 rpm and 70° C. under argon. After 24 h, polystyrene colloid solution was obtained.

18 mL of polystyrene colloid solution was mixed with 240 mL of ethanol and 12 mL ammonia solution (NH$_4$OH) (25 wt %). Then, 3.18 mL of TEOS in 5 mL of ethanol was added dropwise, and the mixture was stirred at 50° C. for 24 h. The solid was collected by centrifugation and calcinated at 550° C. to form hollow silica particles. The average diameter of the pores in the silica shells is 1.49 nm. The surface area and the total pore volume of hollow silica are 193 m$^2$/g and 0.21 cm$^3$/g obtained using the BET and BJH methods, respectively.

Example 2: Preparation of Hollow Silica Particles Functionalized with Amino Groups (HSilica-NH$_2$)

Typically 2 g of hollow silica was dispersed in 90 mL of p-xylene. After 4 mL of N-[3-(trimethoxysilyl)]propyl ethylene diamines (TMSPEA) was added, the solution was kept at 90° C. under argon under stirring for 24 h. The solution was precipitated in ether, and the solid was collected by filtration and was purified by washing with ether.

Example 3: Preparation of Methyl PEG 4-Nitrophenyl Carbonate 10 g of methyl PEG monoether (Mn 5 kDa) was dissolved in 100 mL of dichloromethane. Then 1.2 g of 4-nitrophenyl chloroformate and 0.82 mL of triethylamine were added respectively. The solution was stirred at ambient temperature for 7 days. The crude product was purified by recrystallization from chloroformdiethyl ether.

NMR (CDCl$_3$): δ58.91 (OCH$_3$), δ68.25, 68.54, 70.50, 70.64, 70.90, 71.87 (OCH$_2$CH$_2$), δ121.75, 125.20, 145.32, 152.37 (aromatic), δ155.49 (OCOO).

Example 4: Preparation of PEG-g-Hollow Silica Vesicles

In a glass flask, 0.8 g of TMSPEA attached hollow silica spheres were mixed with 7.2 g of PEG 4-nitrophenyl carbonate in 100 mL of dimethylsulfone. Then the mixture was heated at 80° C. under argon for 2 days. After cooling down, the solution was dispersed in DI water, and the solid was collected using centrifugation followed by washing with DI water for 6 times and drying under vacuum at 50° C.

Example 5: Loading of Calcein Blue into Interpolymer Complex Coated Hollow Silica Vesicles 20 mg of PEG-g-hollow silica was dispersed in 3 mL of DI $H_2O$ (pH 7.4), followed by dissolving 1.0 mg of calcein blue in the solution. pH of the solution was adjusted to pH 7.4 by adding adequate amount of 1.0 M sodium hydroxide solution (NaOH). The solution was sonicated for an hour, and then it was vortexed for 2 days.

Subsequently, 82 µL of 30 wt % PMAA sodium salt solution (Mn: 6.5K or 15K) or 19 mg of PMAA (Mn: 100K) was added to the solution. pH of the solution was then progressively adjusted from pH 8.5, 7.0, 6.0, 5.0, 3.0 until pH reaches 2.0 by adding 1M hydrochloric acid (HCl) solution after solution was being sonicated for 30 min every time once pH was changed.

The solution was then vortexed overnight. After that, calcein blue loaded PMAA/PEG-g-hollow silica was washed with pH 2.0 DI water to remove unloaded calcein blue with aid of centrifugation (9000 rpm, 30 min). Sample was washed until fluorescent intensity of supernatant solution was stable at low intensity.

Example 6: Monitoring Release Profile of Calcein Blue from PMAA/PEG-g-Hollow Silica Complex Calcein blue loaded PMAA/PEG-g-hollow silica was dispersed in 50 mL of pH 2.0 DI water. The release profile at pH 2.0 was monitored first. At designed time intervals, 1.5 mL of the solution was taken out and diluted with 3.5 mL of pH 2.0 DI water. The mixture was filtered through membranes with pores of diameter of 0.22 µm to separate PMAA/PEG-g-hollow silica. Then the fluorescence intensity of the filtrate was measured at 440 nm with an irradiation at 322 nm. After the release profile at acid condition was measured, pH of the solution was adjusted to 7.4. Release profile at neutral pH was measured similarly as abovementioned procedure.

In order to evaluate the interaction of interpolymer complex of PMAA/PEG with calcein blue, a controlled experiment was performed. 3.85 mg of free PEG (Mn: 4.6K) was dispersed in 3 mL of DI $H_2O$ (pH 7.4). Then 0.5 mg of calcein blue was mixed with the solution and was adjusted to pH 7.4. After the solution was stirred for 48 h, 7.53 mg of PMAA (Mn: 100K) or 24 µL of 30 wt % PMAA sodium salt solution (Mw: 6.5 K or 15 K) was added. It was followed by adjusting pH of the solution to pH 2.0. The solution was being vortexed for 24 h. Subsequently the solid was collected by centrifugation and washed with fresh pH 2.0 DI water to remove loosely-bound calcein blue.

To measure the release profile of calcein blue, the solid obtained was dispersed in 50 mL of pH 2.0 DI water. The release profile at pH 2.0 was monitored first. At predetermined time intervals, 1.5 mL of the solution was taken out and diluted with, 3.5 mL of pH 2.0 DI water. The mixture was filtrated through membranes with pores of diameter of 0.22 µm to separate PMAA/PEG polymer complex. Then the fluorescence intensity of the filtrate was measured at 437 nm with an irradiation at 322 nm.

After the release profile at acid condition was measured, pH of the solution was adjusted to 7.4. Release profile at neutral pH was measured similarly as abovementioned procedure.

Example 7: pH Dependence of Release Rate of Calcein Blue from PMAA/PEG-g-Hollow Silica Vesicles Four sets of 20 mg of PEG-g-hollow silica was mixed with 1.0 mg of calcein blue in 3 mL of DI $H_2O$ (pH 7.4). pH of each sample was adjusted to pH 7.4 by adding adequate amount of 1M sodium hydroxide solution (NaOH). The solution was being sonicated for an hour, and then it was vortexed for 2 days. 41 uL of 30 wt % PMAA sodium salt solution (Mn: 6.5K) was then added to each solution. pH of the solution was then slowly adjusted from pH 8.5 to pH 2.0 by adding 1 M hydrochloric acid (HCl) solution after solution was being sonicated. Subsequently, the solution was vortexed overnight. After that, calcein blue loaded PMAA/PEG-g-hollow silica samples were washed with pH 2.0 DI water to remove unloaded calcein blue with aid of centrifugation (9000 rpm, 30 min).

Sample was washed until fluorescent intensity of supernatant solution was stable at low intensity. Sample was then transferred to bottles with 50 mL pH 1.8, 4.0, 6.0 and 7.4 solution, respectively, stirring continuously at low speed. Solution was collected from respective bottles at predetermined time interval and was characterized using fluorescent spectrometer. Solution was excited at wavelength of 322 nm and intensity was detected at 440 nm.

Example 8: Disassociation Kinetic of Interpolymer Complex of PMAA/PEG Coated Hollow Silica Vesicles MAA dissociating from PEG-g-hollow silica vesicles on immersion duration at neutral environment. 40 mg of PEG-g-hollow silica was dispersed in 3 mL HPLC grade water containing 164 µL of 6.5 K PMAA solution. The mixture was being sonicated for an hour. pH of the solution was then slowly adjusted from pH 8.0 to pH 2.0 by adding 1 M hydrochloric acid (HCl) solution after solution was sonicated. Solution was then left stirring for a day. It was then followed by removing solution and precipitant was transferred to 50 mL centrifuge tube containing 50 mL of DI water (pH 7.4). At designated time interval, sample was centrifuged at 10 K rpm for 5 minutes. Supernatant was then discarded and a portion of solid was characterized by $^1$HNMR.

Example 9: Results and Discussion

PEG and PMAA can form polymer complexes via hydrogen-bonding, so it can be expected that PEG/PMAA complexes coated hollow silica vesicles can be obtained by coating PEG-g-hollow silica vesicles with PMAA or coating PMAA-g-hollow silica vesicles with PEG. PMAA-g-hollow silica vesicles reported was explored for this purpose by mixing PEG with sodium PMAA-g-hollow silica vesicles followed by adjusting pH to 3. However, the vesicles obtained could not encapsulate calcium blue. But pH-responsive PMAA/PEG-g-hollow silica vesicles could be produced by coating PEG-g-hollow silica vesicles reported with PMAA. PMAA/PEG-g-hollow silica vesicles were obtained by mixing sodium PMAA mixed with PEG-g-hollow silica vesicles in aqueous solution first followed by adjusting pH of the aqueous solution to pH 2. Sodium PMAA of a molecular weight (MW) of 6.5 K, 15 K and 100 K described as 6.5 K PMAA, 15 K PMAA and 100 K PMAA are used respectively.

Example 10: Formation and Structures of PMAA/PEG-Graft-Hollow Silica Vesicles

Figure 4:
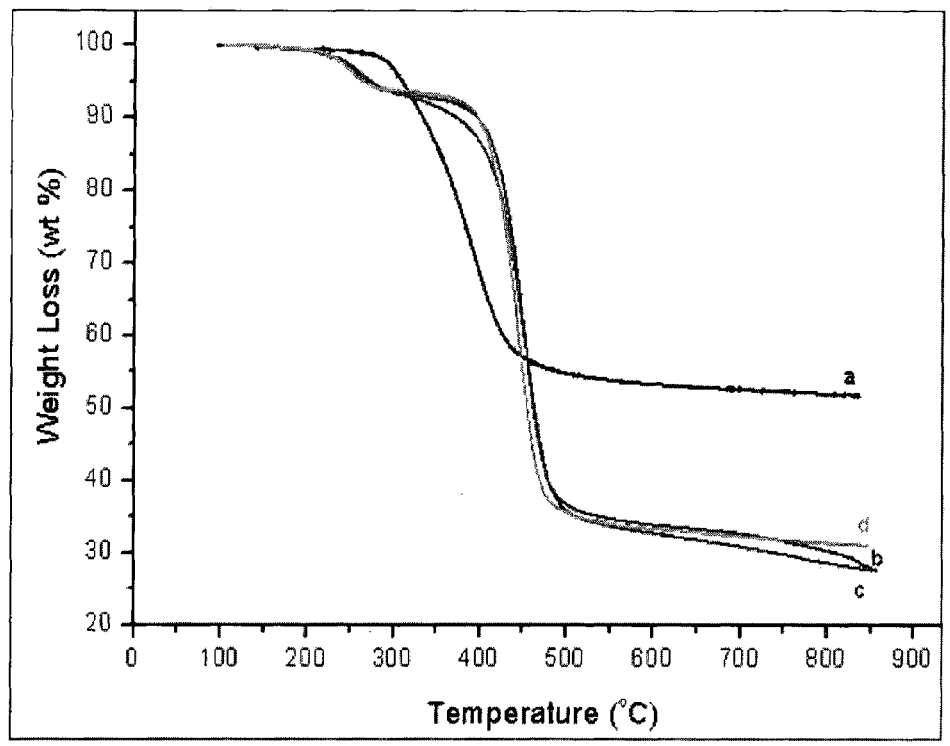
FIG. 4 is a graph showing thermogravimetric analysis (TGA) curves of (a) PEG-g-hollow silica vesicles; and PMAA incorporated PEG-g-hollow silica hybrids with PMAA molecular weight of (b) 6.5 K; (c) 15 K; and (d) 100 K. Y-axis: weight loss (%) and x-axis: temperature (° C.).

The composition of PMAA/PEG-g-hollow silica can be determined using TGA. FIG. 4 illustrates the TGA curves (a) to (d) of PEG-g-hollow silica vesicles and PMAA/PEG-g-hollow silica with different PMAA molecular weight. Referring to FIG. 4, the content of PEG in PEG-g-hollow silica was determined to be about 46 wt % from (a) as reported before. Then the increased weight loss of PMAA/PEG-g-hollow silica vesicles as shown in (b) to (d) at 750° C. are PMAA content in PMAA/PEG-g-hollow silica. PMAA content is about 21 wt %, 23 wt % and 21 wt % in 6.5 K, 15 K and 100 K PMAA/PEG-g-hollow silica vesicles, respectively. On the basis of these results, the molar ratio of MAA unit in PMAA to EG unit in PEG can be calculated to be ca. 1:3.4, 1:3.1, and 1:3.4 respectively.

Theoretically, the perfect PMAA/PEG complexes are composed of MAA units and EG units with a molar ratio of 1:1. Only less than ⅓ of EG units in PEG brushes on the hollow silica spheres forms hydrogen bonding with MAA units from PMAA in the PMAA/PEG complexes.

On the other hand, Mw of PMAA chains shows insignificant effects on the amount of PMAA to be introduced into the PMAA/PEG complex layers formed on the hollow silica spheres surfaces. So it can be assumed that not all EG units grafted on the hollow silica spheres surfaces can be accessed by anionic PMAA chains due to steric hindrance, and outside EG units of PEG brushes form complex with PMAA.

Figure 3:
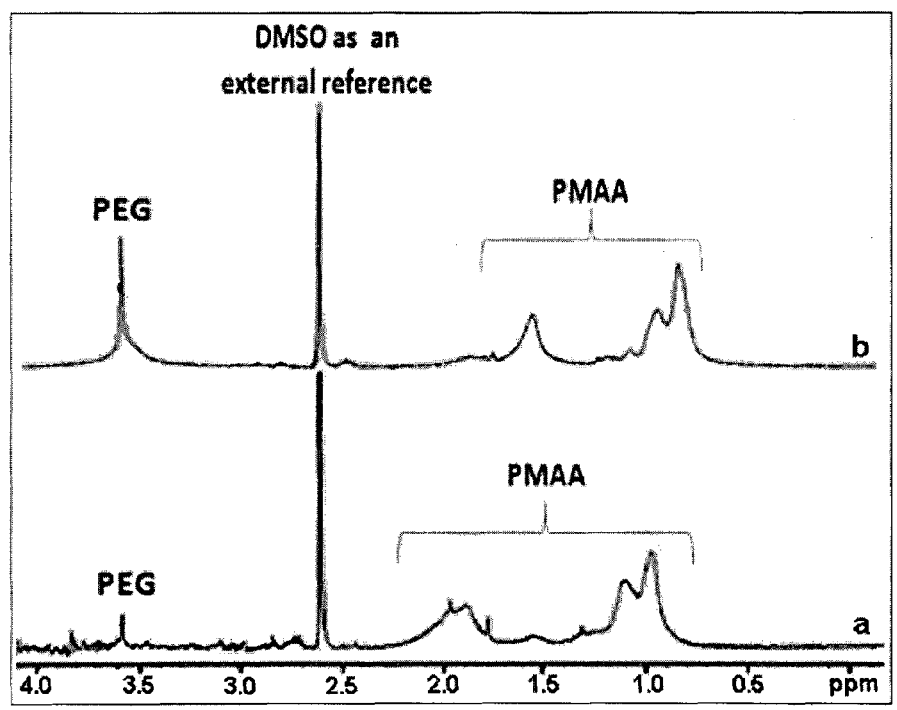
FIG. 3 is a graph showing 1H NMR spectra of PMAA 6.5 K/PEG-g-hollow silica nanoparticles at (a) pH 2; and (b) pH 7. DMSO was used as an external reference.

The formation of PMAA/PEG complex on the hollow silica spheres were monitored using $^1$H NMR. Sodium PMAA (Mw: 6.5 K) and PEG-g-hollow silica vesicles with the molar ratio of MAA unit to EG unit to be 1:1 was mixed in D$_2$O at pH 8.9 followed by adjusting pH to 2.6. FIGS. 3 (*a*) and (*b*) are $^1$H NMR spectra of the solution obtained at pH 8.9 and 2.6 respectively.

Meanwhile, the peak attributed to protons of PMAA chains becomes broader together with a downfield shift in position similar to that observed before for PMAA-g-hollow silica vesicles. Quantitatively the integrated intensity ratio of PMAA proton peaks with respect to those of external reference DMSO decreases from 10.3 to 4.8 by 215%.

In contrast, the decrease in peak intensity of PMAA in PMAA-g-hollow silica vesicles is by 181%. The higher decrease in the peak intensity of protons attribute to PMAA in aqueous solution of PMAA/PEG-g-hollow silica vesicles is due to formation of complexes between PMAA and PEG, and reflects that PMAA/PEG complex layer is denser than PMAA layers only on hollow silica spheres. So it can be expected that PMAA/PEG complex layers provide more secure encapsulation than PMAA layers.

On the other hand, the peak attributed to protons of PEG almost disappeared at pH from 8.9 to 2.6 as shown in FIG. 3 (*b*). This indicates that almost all of the PEG units are locked with much reduced chain mobility after PMAA/PEG complex was formed. However, TGA results indicate that only a few more than ⅓ of EG units in PEG brushes formed complex with PMAA. The disappearance of the peaks of protons attributed to the residual EG units should be caused by that 1) originally these EG units adjacent to the hollow silica surfaces cannot show signal in $^1$H NMR spectrum due to low mobility or difficult access to water; or 2) the PMAA/PEG complex layers assumed formed as outmost layers prevent the access of water to the residual EG units inside. These free EG units layers should also provide encapsulation function due to the low mobility.

Figure 2:
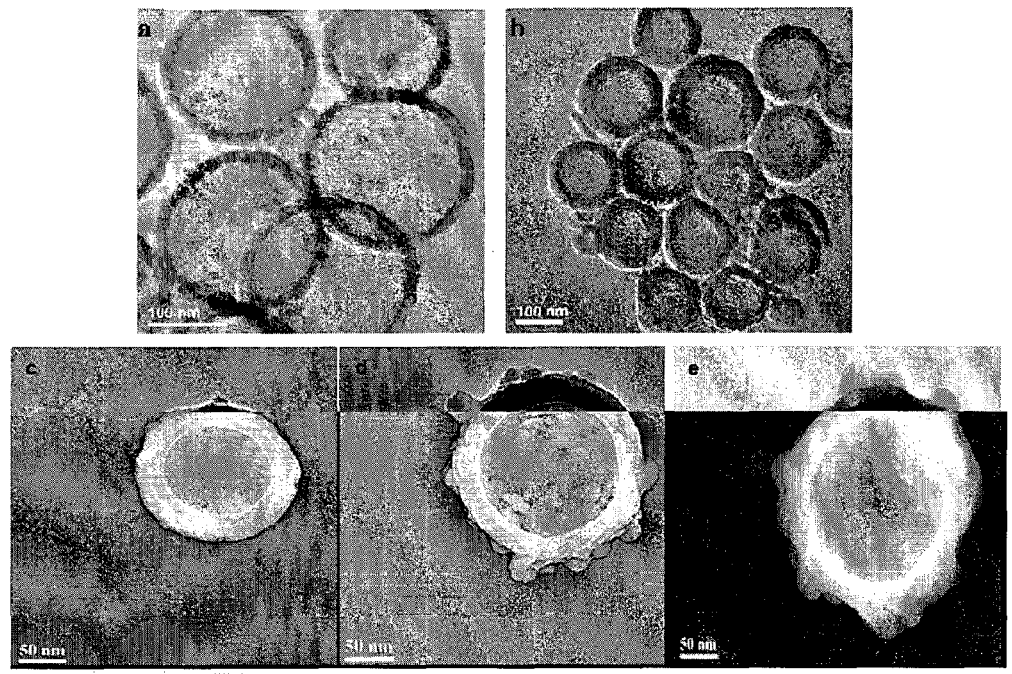
FIG. 2 shows transmission electron microscopy (TEM) micrographs of (a) pristine hollow silica spheres; (b) PEG-g-hollow silica vesicles; and PMAA/PEG-g-hollow silica vesicles with PMAA molecular weight of (c) 6.5 K, (d) 15 K, and (e) 100 K. Scale bar in (a) and (b) denotes a length of 100 nm; scale bar in (c) to (d) denotes a length of 50 nm.
Figure 5:
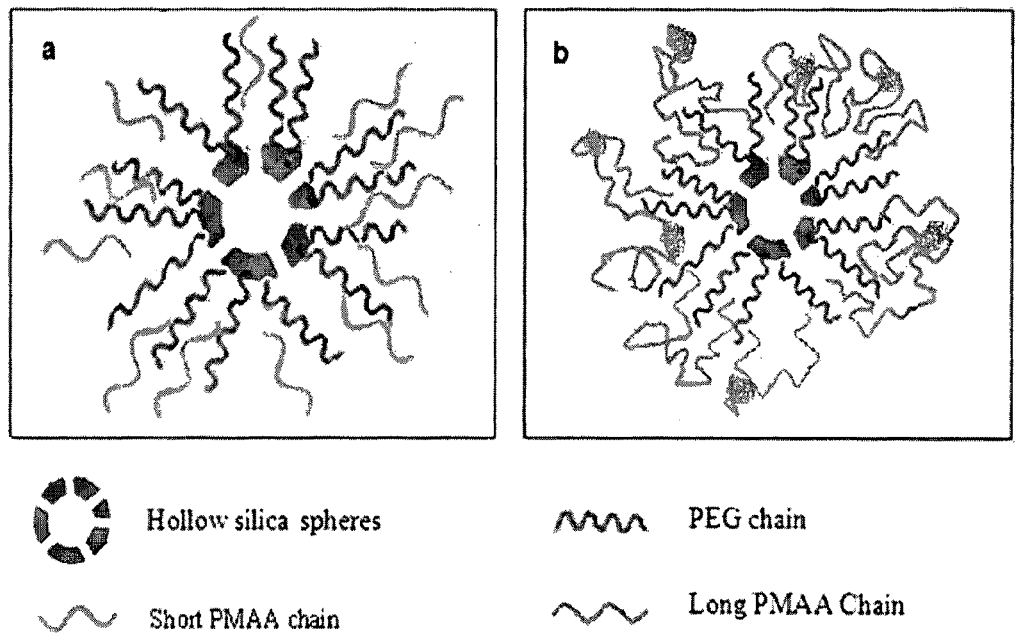
FIG. 5 is a schematic diagram showing interaction between PEG-g-hollow silica vesicle and (a) short/low molecular weight PMAA; and (b) long/high molecular weight PMAA.
Figure 6:
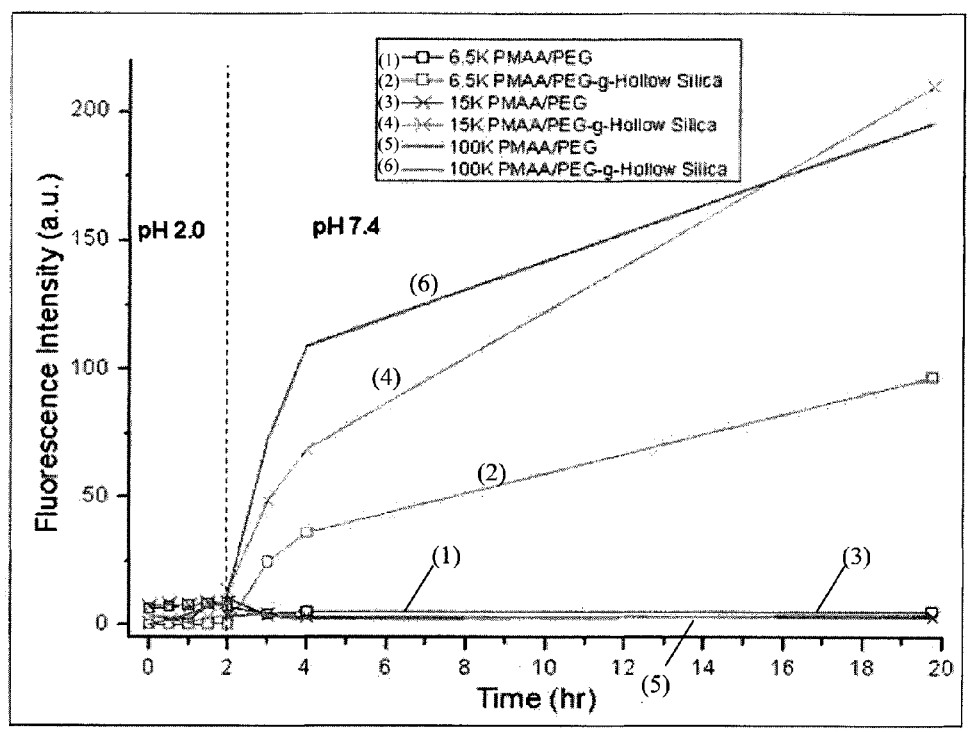
FIG. 6 is a graph showing release profiles of calcein blue from PMAA/PEG-g-hollow silica hybrids and PMAA/PEG interpolymer complexes with PMAA molecular weight of (a) 6.5 K; (b) 15 K; and (c) 100 K. Y-axis: fluorescence intensity (a.u.) and x-axis: time (hr).

Morphology of PMAA/PEG-g-hollow silica vesicles were investigated using TEM. FIG. 2. shows the images of pristine hollow silica and PMAA/PEG coated hollow silica vesicles. In comparison with TEM images of pristine hollow silica (FIG. 2(*a*)) and PEG-g-hollow silica vesicles (FIG. 2(*b*)), PMAA/PEG interpolymer complex layers of PMAA/PEG-g-hollow silica vesicles from PMAA of different MW can be observed obviously (FIGS. 2(*c*), (*d*) and (*e*)). Note that surface roughness of vesicles increases with MW of PMAA as shown in FIGS. 2(*c*), (*d*) and (*e*). This should be due to the different feasibility of PMAA chains in forming zipper/ladder-like cooperative interaction with PEG chains on silica surface. PEG-g-hollow silica vesicles have very restricted space on surface to be occupied by PMAA chains. Therefore, in order to produce ladder like cooperative interaction with PEG chains, PMAA chains must have great flexibility to occupy gaps between PEG chains attached on hollow silica surface. As depicted in FIG. 5*a*, 6.5 K PMAA has good flexibility and can intrude gaps between PEG brushes chains on hollow silica spheres surfaces to form well matched layer-by-layer interaction between PMAA chains and PEG chains, which will provide compact and smooth PMAA/PEG complex layers. However, 15 K PMAA and 100 kDa PMAA chains should have a lower flexibility in accommodating limited space between PEG chains even in outside parts of PEG brushes as assumed, and it is highly possible that PMAA chains lumps are formed results which result in rough PMAA/PEG complex layers as depicted in FIG. 5*b*.

Consequently, coverage of interpolymer complex layer on hollow silica surface becomes irregular and lumpy.

Example 11: pH-Responsive Encapsulation and Release of Water Soluble Calcein Blue Calcein blue was utilized as a typical water soluble species to investigate competency of PMAA/PEG-g-hollow silica vesicles as pH-responsive vesicles. To load Calcein blue, it was dissolved in aqueous solution of PEG-g-hollow silica vesicles at pH 7.4 and the solution was vortexed for 2 days under ambient condition for sufficient diffusion of calcein blue into the interiors of hollow silica spheres. Certain amount of sodium PMAA was added and pH was adjusted gradually to pH 2. to facilitating the formation of PMAA/PEG complex to seal the pores in the hollow silica shell for encapsulation of calcein blue loaded.

The pH-responsive release profiles of calcein blue from PMAA-PEG-g-hollow silica vesicles were monitored and are presented in FIG. 6 with an incubation time of 20 h at pH 2.0 respectively. FIG. 6 reflect that PMAA/PEG complex can provide secure encapsulation of calcein blue at pH 2. However, calcein blue is released out when pH is adjusted to 7.4. This is caused by the disassociation of PMAA/PEG complex on the surface of hollow silica surface resulting in the open of the pores in the silica shell for calcein blue release. Furthermore it is indicated that the release profile of PMAA/PEG-g-hollow silica vesicles at pH 7.4 can be adjusted by using PMAA with different molecular weight. Surprisingly, 6.5 k PMAA provides a slower release than 15 k PMAA and 100 k PMAA.

In order to understand the slow release profiles of PMAA (6.5 kDa) PMAA/PEG-g-hollow silica vesicles, the disassociation kinetic of the PMAA (6.5 kDa)/PEG complex were investigated using $^1$H NMR. PMAA/PEG complex layers on the surface of hollow silica spheres disassemble when pH is changed to certain pH at which deprotonation of carboxylic acid groups in PMAA occurs leading to breakdown of the hydrogen bonding between the carboxylic acid groups in PMAA and the ether groups in PEG. This results in dissolving of soluble PMAA salt in aqueous solution. Therefore the remaining PMAA in PMAA/PEG-g-hollow silica vesicles can be measured to indicate the disassociation kinetic. Therefore, pH of PMAA (6.5 kDa)/PEG-g-hollow silica vesicles aqueous solution was adjusted to 7.4, and the solutions were centrifuged at a certain time interval with supernatant containing the released PMAA being discarded and the precipitated part being dissolved in $D_2O$ for NMR characterization. The percentage of PMAA remained in the PMAA/PEG complex may be calculated using equation 1:

$$\text{Residual PMAA w/w \%} = I_{0.96}/3 \times 86/(I_{0.96}/3 \times 86 + I_{3.59}/2 \times 44) \times 100\%$$

where $I_{0.96}$ and $I_{3.59}$ are the integral intensity of peaks at 0.96 ppm and 3.59 ppm attributed to protons of methyl units in PMAA and EG units in PEG respectively.

Figure 8:
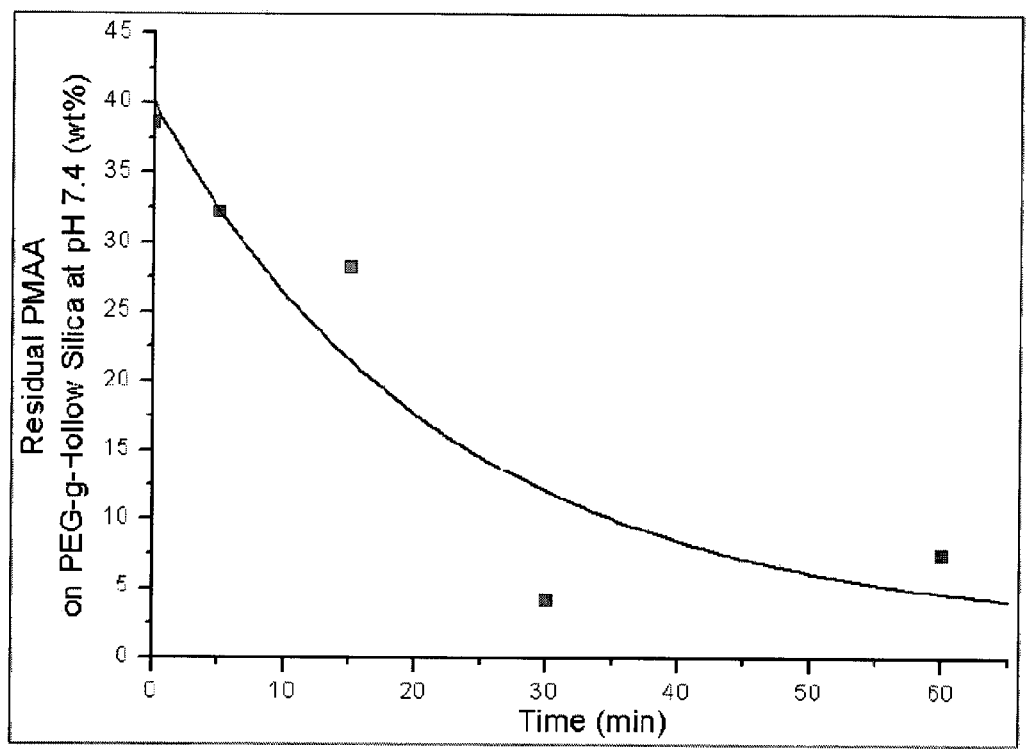
FIG. 8 is a graph showing relative amount of PMAA chains that remain attached on PEG-g-hollow silica vesicles as a function of immersion duration in neutral environment.

Time dependence of percentage of PMAA remained in the PMAA/PEG complex is presented in FIG. 8. The results reflect that the disassociation of PMAA and PEG complex formed on the hollow silica spheres surfaces is not instantaneous at pH 7.4. The disassociation of PMAA/PEG complex should be comprised of deprotonation of PMAA leading to breakdown of hydrogen bonding between MAA and EG, swelling of the complex and dissolving of anionic PMAA. The swelling should be the detrimental step of the disassociation, a complex of PMAA/PEG with a higher integrity would disassociate slower, and a slow release profile would be observed.

Figure 7:
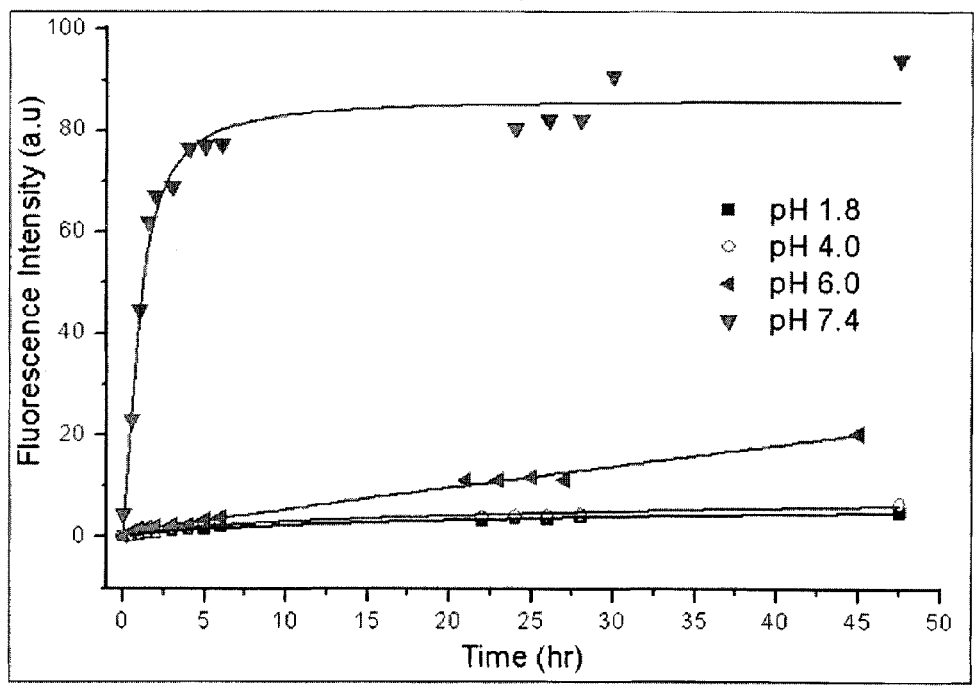
FIG. 7 is a graph showing dependence of release profile on solution pH for calcein blue loaded with PMAA/PEG-g-hollow silica vesicles with PMAA molecular weight of 6.5 K. Y-axis: fluorescence intensity (a.u.) and x-axis: time (hr).

From TEM results, it is rational to state that 6.5 K PMAA provides more compact PMAA/PEG layers on the hollow silica sphere surfaces. Hence PMAA (6.5 K)/PEG-g-hollow silica vesicles shows the slowest release. Further pH effect on the release profile of calcein blue from 6.5 K PMAA/PEG-g-hollow silica vesicles was investigated, and the typical results are shown in FIG. 7.

At pH 1.8 and 4.0, compact PMAA/PEG complex layers are on the surfaces of hollow silica spheres similar to that at pH 2.0 above, so the pores in the silica shells are sealed well and almost no calcein blue can escape from the vesicles. At pH 6.0, a little more calcein blue was released after 45 h. This reflects that the PMAA/PEG complex layers become less dense but the pores in the silica shells are still covered by the PMAA/PEG complex layers. However, it is observed that much more calcein blue is released at pH 7.4 as discussed above.

In conclusion, PMAA/PEG complex coated hollow silica vesicles can be obtained from PEG-g-hollow silica vesicles and PMAA. The molar ratio of MAA units in PMAA and EG units in PEG brushes is around 1:3 rather than 1:1, probably due to that EG units in the outside layers of PEG brushed accessible to PMAA anionic chain for the steric hindrance on the hollow silica spheres. However the residual EG units have very low mobility or poor accessibility to water. Both PMAA/PEG complex layers and PEG layers without forming complex should provide sealing function to the pores in the hollow silica shells.

PMAA with a lower Mw provides a more compact. PMAA/PEG layers probably due to the better feasibility to matching EG units on the crowd PEG brushes on the hollow silica surfaces. Although all the PMAA/PEG complex layers from 6.5 K, 15 K and 100 K PMAA provide secure encapsulation capability of calcein under acidic condition, the slowest release of calcein from PMAA (6.5 K)/PEG-ghollow silica vesicles was observed.

PMAA/PEG-g-hollow silica vesicles have secure encapsulation capability at acidic condition, and probable an inner PEG covering inner interiors good for protecting sensitive species, and adjustable release profiles together with releasing PEG-g-hollow silica vesicles under pH 7.4. These features render PMAA/PEG-g-hollow silica vesicles promising for many applications including for formulation of safe and efficient oral administration systems for drugs, proteins, genes and nutrients.

In various embodiments, poly(methacrylic acid)/poly(ethylene glycol)-graft-hollow silica (PMAA/PEG-g-HSi) vesicles have been obtained. Neutral PMAA may form interpolymer complex with PEG through hydrogen bonding between carboxylic acid groups and ether units. PMAA/PEG complex on the hollow silica surfaces is denser than free PMAA layer, thereby providing a more secure and stable encapsulation as compared to PMAA-g-hollow silica vesicles. In addition, PEG-g-hollow silica vesicles can be released out at a pH value of about 7.4, which can functionalize as an in-situ formed delivery system with PEG stealth layers and hollow silica spheres. Hence, PMAA/PEG-g-hollow silica vesicles are expected to provide unique encapsulation and delivery performances which cannot be obtained from these currently available encapsulation and delivery systems.

New types of stimuli-responsive vesicles have been produced. The vesicles are able to provide secure encapsulation of various species through forming PMAA/PEG complex for coating hollow silica spheres. Meanwhile, PEG-g-hollow silica vesicles for further encapsulation and delivery of loaded species may be formed in-situ when pH is adjusted to deprotonate PMAA.

Furthermore, PMAA/PEG complex layer is denser than free PMAA layer, therefore is able to provide more secure encapsulation of loaded species under pH with neutral PMAA being formed.

PEG-g-hollow silica vesicles may be formed in situ under pH with sodium PMAA being formed. PMAA/PEG-g-hollow silica vesicles are promising for safe and efficient oral administration of nutrients and drugs. The vesicles may hold and protect drugs in acidic stomach, but species which are loaded in PEG-g-hollow silica vesicles may be released out at intestine with pH around of 7.4. PEG stealth layers are able to enhance paracellular permeability through epithelial cell monolayers, by enlarging interstitial space of tight junctions which promotes absorption efficacy of therapeutic agents. After entering blood stream, PEG stealth layers may render species loaded with long circulation time which will facilitate passive targeting.

To produce pH responsive vesicles for secure encapsulation of various species under pH with neutral PMAA being formed, however, PEG-g-hollow silica vesicles with encapsulated species are formed under pH with deprotonated PMAA being formed.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of preparing a porous hollow silica particle with a pH responsive interpolymer complex immobilized thereon, the method comprising:
   a) providing a suspension comprising a porous hollow silica particle having a first polymer immobilized thereon;
   b) adding a solution comprising a second polymer to the suspension to form a mixture, the second polymer selected from the group consisting of poly(methacrylic acid) and copolymers thereof and having a molecular weight in the range of from 3 kDa to 8 kDa; and
   c) complexing the second polymer with the first polymer to form an interpolymer complex, wherein the interpolymer complex forms a layer round the silica particle and depending on the pH of the environment within which the silica particle is placed, the structure of the interpolymer complex layer assumes a closed or collapsed structure in which the pores of the silica particle are covered or an open structure in which the pores of the silica particle are not covered.

2. The method according to claim 1, wherein the poly (methacrylic acid) is of the general formula (1)

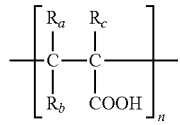 (1)

wherein $R_a$, $R_b$ and $R_c$ are independently an aliphatic, an alicyclic, an aromatic or an arylaliphatic group with a main chain of about 1 to about 30 carbon atoms and 0 to about 10 heteroatoms selected from the group consisting of N, O, S, Se and Si; and n is an integer from 2 to 10000; wherein all groups may be optionally substituted.

3. The method according to claim 1, wherein the copolymers comprise copolymers from poly(methacrylic acid) of general formula (1) and vinyl monomers of the general formula (2)

$$CH_2=CR_xR_y \qquad (2)$$

wherein in formula (2), $R_x$ and $R_y$ are each independently selected from the group consisting of H, optionally substituted aliphatic, an alicyclic, an aromatic and an arylaliphatic group with a main chain of about 1 to about 30 carbon atoms and 0 to about 10 heteroatoms selected from the group consisting of N, O, S, Se and Si.

4. The method according to claim 1, wherein the second polymer is complexed with the first polymer by hydrogen bonding.

5. The method according to claim 4, wherein the first polymer is a polar polymer capable of forming a hydrogen bond with the second polymer.

6. The method according to claim 1, wherein the first polymer is selected from the group consisting of poly (ethylene glycol), poly(vinyl pyrrolidone), chitosan, derivatives thereof, and copolymers thereof.

7. The method according to claim 1, wherein the second polymer has a molecular weight of 6.5 kDa.

* * * * *

UNITED STATES PATENT AND TRADEMARK OFFICE
CERTIFICATE OF CORRECTION

PATENT NO. : 10,022,332 B2
APPLICATION NO. : 14/417107
DATED : July 17, 2018
INVENTOR(S) : Liu et al.

Page 1 of 1

It is certified that error appears in the above-identified patent and that said Letters Patent is hereby corrected as shown below:

On the Title Page

At item (30):
Delete "Jul. 25, 2012 (SG) .....................201205535" and
Insert -- Jul. 25, 2012 (SG) .....................201205535-6 --.

Signed and Sealed this
Eleventh Day of December, 2018

Andrei Iancu
*Director of the United States Patent and Trademark Office*